(12) United States Patent
Mindich et al.

(10) Patent No.: US 11,840,531 B2
(45) Date of Patent: Dec. 12, 2023

(54) CDK8/19 INHIBITORS

(71) Applicant: JOINT STOCK COMPANY "BIOCAD", St. Petersburg (RU)

(72) Inventors: Aleksei Leonidovich Mindich, St. Petersburg (RU); Anna Jur'evna Chestnova, G. Gatchina (RU); Mariia Andreevna Kasatkina, G. Krasnodar (RU); Andrei Ivanovich Alafinov, G. Vsevolozhsk (RU); Aleksei Sergeevich Gavrilov, St. Petersburg (RU); Anton Aleksandrovich Evdokimov, St. Petersburg (RU); Liliana Vyacheslavovna Lenshmidt, St. Petersburg (RU); Elena Aleksandrovna Maksimenko, St. Petersburg (RU); Mariia Sergeevna Mishina, St. Petersburg (RU); Sergei Aleksandrovich Silonov, G. Samara (RU); Evgenii Jur'evich Smirnov, St. Petersburg (RU); Pavel Andreevich Iakovlev, St. Petersburg (RU); Dmitry Valentinovich Morozov, St. Petersburg (RU)

(*) Notice: Subject to any disclaimer, the term of this patent is extended or adjusted under 35 U.S.C. 154(b) by 238 days.

(21) Appl. No.: 17/264,670

(22) PCT Filed: Jul. 31, 2019

(86) PCT No.: PCT/RU2019/050123
§ 371 (c)(1),
(2) Date: Jan. 29, 2021

(87) PCT Pub. No.: WO2020/027704
PCT Pub. Date: Feb. 6, 2020

(65) Prior Publication Data
US 2021/0246138 A1 Aug. 12, 2021

(30) Foreign Application Priority Data
Aug. 3, 2018 (RU) ................................ 2018128415

(51) Int. Cl.
*C07D 471/04* (2006.01)
*A61P 35/00* (2006.01)
*A61K 31/4375* (2006.01)

(52) U.S. Cl.
CPC ........ *C07D 471/04* (2013.01); *A61K 31/4375* (2013.01); *A61P 35/00* (2018.01)

(58) Field of Classification Search
CPC .. A61P 35/00; A61P 7/02; A61P 35/02; C07D 471/04; A61K 31/4375
See application file for complete search history.

(56) References Cited

U.S. PATENT DOCUMENTS

2016/0016951 A1  1/2016  Schemann et al.

FOREIGN PATENT DOCUMENTS

| JP | 2009-532486 A | 9/2009 |
| JP | 2011-506336 A | 3/2011 |
| JP | 2017-522324 A | 8/2017 |
| WO | 2015/014768 A1 | 2/2015 |
| WO | 2016/009076 A1 | 1/2016 |
| WO | 2017/202719 A1 | 11/2017 |

OTHER PUBLICATIONS

Corresponding Australian application No. 2019313199 Examination report dated Oct. 17, 2022.
Wu Xu et al., Dysregulation of CDK8 and Cyclin C in tumorigenesis. Journal of Genetics and Genomics, vol. 38, Issue 10, Oct. 20, 2011, pp. 439-452.
Galbraith, M. D., et al. CDK8. A positive regulator of transcription. Transcription, vol. 1, 2010—Issue 1.
Firestein, R. & Hahn, W. C., Revving the Throttle on an Oncogene: CDK8 Takes the Driver Seat. Cancer research, Oct. 2009, vol. 69, Issue 20.
Adler, A. S., et al. CDK8 maintains tumor de-differentiation and embryonic stem cell pluripotency, Cancer research, Apr. 2012, vol. 72, Issue 8, 2129-2139.

(Continued)

*Primary Examiner* — Kortney L. Klinkel
*Assistant Examiner* — Padmaja S Rao

(57) ABSTRACT

The present invention relates to novel compounds of formula I:

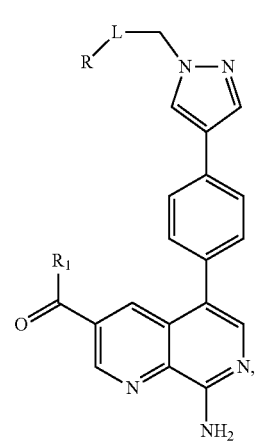

which have the properties of CDK8/19 inhibitors, to a pharmaceutical composition comprising said compounds, and to use thereof as a medicine for treating diseases and disorders.

15 Claims, No Drawings

(56) References Cited

OTHER PUBLICATIONS

Kapoor, A., et al. The histone variant macroH2A suppresses melanoma progression through regulation of CDK8, Nature vol. 468, pp. 1105-1109 (2010).

Firestein, R., et al., CDK8 is a colorectal cancer oncogene that regulates β-catenin activity. Nature vol. 455, pp. 547-551 (2008).

Firestein, R., et al. CDK8 expression in 470 colorectal cancers in relation to β-catenin activation, other molecular alterations and patient survival. vol. 126, Issue12, Jun. 15, 2010, pp. 2863-2873.

Broude E., et al., Expression of CDK8 and CDK8-interacting Genes as Potential Biomarkers in Breast Cancer. Current Cancer Drug Targets, vol. 15, No. 8, 2015, pp. 739-749(11).

Gyorffy, B., et al., An online survival analysis tool to rapidly assess the effect of 22,277 genes on breast cancer prognosis using microarray data of 1,809 patients. Breast Cancer Research and Treatment vol. 123, pp. 725-731 (2010).

Alarcon, C, et al., Nuclear CDKs Drive Smad Transcriptional Activation and Turnover in BMP and TGF-β Pathways, Cell, vol. 139, Issue 4, Nov. 13, 2009, pp. 757-769.

DiDonato, J. A., et al. (2012) NF-κB and the link between inflammation and cancer, Immunological Reviews. vol. 246, Issue1, Special Issue: NF-Kb, Mar. 2012, pp. 379-400.

Acharyya, S., et al., A CXCL1 paracrine network links cancer chemoresistance and metastasis, Cell, vol. 150, Issue 1, Jul. 6, 2012, pp. 165-178.

Fabian et al. (2005) A small molecule-kinase interaction map for clinical kinase inhibitors, Nature Biotechnology vol. 23, pp. 329-336 (2005).

Huang, et al. (2012) MED12 Controls the response to multiple cancer drugs through regulation of TGF-β receptor signaling, Cell, vol. 151, Issue 5, Nov. 21, 2012, pp. 937-950.

Stephen M. Berge et al., Pharmaceutical Salts. J Pharm Sci. Jan. 1977;66(1):1-19.

International application No. PCT/RU2019/050123 International Search Report dated Nov. 28, 2019.

International application No. PCT/RU2019/050123 English translation of International Search Report dated Nov. 28, 2019.

The corresponding European application No. 19844331.9 extended European search report dated Mar. 22, 2022.

Corresponding Japanese application No. 2021-505964 Notice of Refusal dated Apr. 24, 2023.

CDK8/19 INHIBITORS

FIELD OF INVENTION

The present invention relates to novel CDK8/19 inhibitors, methods for their preparations, pharmaceutical compositions comprising the present compounds and methods of using said compounds or said compositions in the treatments of diseases and disorders.

BACKGROUND OF THE INVENTION

CDK8, along with its closely related isoform, in terms of structure and function, CDK19, is an oncogenic transcription regulating kinase (Xu, W. & Ji, J. Y. (2011) Dysregulation of CDK8 and Cyclin C in tumorigenesis, J. Genet. Genomics 38, 439-452; Galbraith, M. D., et al. (2010); Firestein, R. & Hahn, W. C. (2009)). In contrast to CDK1, CDK2 and CDK4/6 kinases, CDK8 plays no role in cell cycle regulation, and, therefore, blocking CDK8 does not suppress the growth of normal cells (Adler, A. S., et al. (2012) CDK8 maintains tumor de-differentiation and embryonic stem cell pluripotency, Cancer Res. 72, 2129-2139; Kapoor, A., et al. (2010) The histone variant macroH2A suppresses melanoma progression through regulation of CDK8, Nature 468, 1105-1109). However, CDK8 knockout in embryonic stem cells prevents embryonic development (Adler, A. S., et al. (2012)) due to its essential role in the formation of the pluripotent stem cell phenotype (Firestein, R., et al. (2008)). The role of CDK8 in carcinogenesis is due to its unique function as a regulator of several transcriptional programs (Xu, W. & Ji, J. Y. (2011)). CDK8 overexpression has been observed in 50% of colon cancers (Firestein, R., et al. (2010)), melanomas (Kapoor, A., et al. (2010)), breast cancers (Broude E., et al. (2015)) and has been associated with poor prognosis (Gyorffy, B., et al. (2010)).

The carcinogenic effect of CDK8 is mediated by positive regulation of Wnt/[beta] signaling pathway (Kapoor, A., et al. (2010); Alarcon, C, et al. (2009) Nuclear CDKs drive Smad transcriptional activation and turnover in BMP and TGF-beta pathways, Cell 139, 757-769), transcription induced by growth factor NF-kB (DiDonato, J. A., et al. (2012) NF-kappaB and the link between inflammation and cancer, Immunol. Rev. 246, 379-400) and activation of TGF-beta signaling pathway (Acharyya, S., et al. (2012) A CXCL1 paracrine network links cancer chemoresistance and metastasis, Cell 150, 165-178). It is known that chemotherapeutic drugs contribute to DNA damage, TNFα induction, activation of the transcription factor NFkB (Fabian et al. (2005) A small molecule-kinase interaction map for clinical kinase inhibitors, Nat. Biotechnol. 23, 329-336). Stroma-derived TNFa acts on tumor cells, where it induces NFkB-mediated production of cytokines CXCL1 and CXCL2 promoting growth of tumor cells. CXCL 1/2 attract myeloid cells to the tumor, by binding to CXCR2 receptor on the myeloid cell surface. Myeloid cells, in turn, secrete S 100A8/9 proteins associated with chronic inflammation and tumor growth (Huang, et al. (2012) MED12 Controls the response to multiple cancer drugs through regulation of TGF-β receptor signaling, Cell 151, 937-950). It was also demonstrated that CDK8 can maintain the pluripotent phenotype of embryonic stem cells and can be associated with the cancer stem cell phenotype (Firestein, R., et al. (2008) CDK8 is a colorectal cancer oncogene that regulates beta-catenin activity, Nature 455, 547-551).

Search of new compounds inhibiting cyclin-dependent protein kinases CDK8/19 is of current interest.

SUMMARY OF INVENTION

The terms used in the description of this invention appear below.

"Alkyl" means an aliphatic straight chain or branched chain hydrocarbon group having from 1 to 12 carbon atoms, more preferably from 1 to 6 carbon atoms. "Branched" chain means alkyl chain having one or more "lower alkyl" substituents. Examples of alkyl groups include, but are not limited to, methyl, ethyl, n-propyl, iso-propyl, n-butyl, iso-butyl, sec-butyl, tert-butyl, n-pentyl, 2-pentyl, 3-pentyl, neo-pentyl, n-hexyl. Alkyl may have substituents which may be same or different structure.

"Alkenyl" means a straight chain or branched chain aliphatic hydrocarbon group having from 1 to 12 carbon atoms, more preferably from 1 to 6 carbon atoms that contains one or more carbon-carbon double bound. Alkenyl may have substituents which may be same or different structure. Exemplary alkenyl groups are, without limitation, vinyl, allyl, 1-methylethenyl, prop-1-enyl, but-1-enyl, but-2-enyl, but-3-enyl, 1-methylprop-1-enyl, 1-methylprop-2-enyl, 2-methylprop-1-enyl, 2-methylprop-2-enyl.

"Alkynyl" means a straight chain or branched chain hydrocarbon group having from 2 to 12 carbon atoms, more preferably from 2 to 6 carbon atoms that contains one or more carbon-carbon triple bound. Alkynyl may have substituents which may be same or different structure. Examples of alkynyl groups include, but are not limited to, ethenyl, propargyl, 1-methylprop-2-ynyl, 2-methylprop-1-enyl, but-1-ynyl, but-2-ynyl, but-3-ynyl.

"Cycloalkyl" means a saturated carbocyclic ring that contains from 3 to 10 carbon ring atoms. Examples of cycloalkyl groups include, but are not limited to, monocyclic groups, such as cyclopropyl, cyclobutyl, cyclopentyl, cyclohexyl, cycloheptyl, cyclooctyl, cyclononyl or cyclodecyl, bicyclic groups, such as bicycloheptyl or bicyclooctyl. Cycloalkyl may have substituents which may be same or different structure.

"Cycloalkenyl" means a non-aromatic carbocyclic ring system comprising 3 to 10 carbon atoms in a cycle, the ring contains one or more carbon-carbon double bonds. Cycloalkenyl may have substituents which may be same or different structure. Examples of cycloalkenyl groups include, but are not limited to, monocyclic groups, such as cyclopropenyl, cyclobutenyl, cyclopentenyl, cyclohexenyl, cycloheptenyl, cyclooctenyl, cyclononenyl or cyclodecenyl.

"Aryl" means an aromatic monocyclic or polycyclic system having from 6 to 14 carbon atoms, more preferably from 6 to 10 carbon atoms. Aryl may have cyclic system substituents which may be same or different structure. Aryl can be annelated with a cycloalkyl, heterocycle or heteroaryl. Examples of aryl groups include, but are not limited to, phenyl, naphthyl, anthranil and the like.

"Alkyloxy" or "Alkoxy" means an alkyl-O— group, wherein alkyl is defined in this section. Examples of alkoxy groups include, but are not limited to, methoxy, ethoxy, n-propoxy, iso-propoxy and n-butoxy.

"Amino group" means a R'R"N— group.

Examples of R' and R" include, but are not limited to, substituents selected from the group comprising hydrogen, alkyl, alkenyl, alkynyl, cycloalkyl, aryl, heterocyclyl, heteroaryl, which are defined herein, or R' and R" together with the nitrogen atom they are attached to, form 4-7-membered heterocyclyl or 5-10-membered heteroaryl.

"Alkylsulfonyl" (—S(O)$_2$—C$_1$-C$_6$alkyl) means "alkyl" as defined above attached to an appropriate molecule fragment through a sulfonyl group —SO$_2$—. Examples of alkyl sulfonyls include, but are not limited to, methylsulfonyl, ethylsulfonyl, etc.

"Lower alkyl" means a straight chain or branched chain alkyl having from 1 to 4 carbon atoms.

"Halo" or "Halogen" (Hal) means fluoro, chloro, bromo and iodo.

"Heterocycle", "heterocyclyl", "heterocyclic ring" means a monocyclic or polycyclic non-aromatic system having from 3 to 11 carbon atoms, of which one or more carbon atoms are substituted by one or more heteroatoms, such as nitrogen, oxygen, sulfur. Heterocycle can be condensed with aryl or heteroaryl. Heterocycle may have one or more substituents which may be same or different structure. Nitrogen and sulfur atoms of heterocycle could be oxidized to N-oxide, S-oxide or S-dioxide. Heterocycle may be fully saturated, partially saturated and unsaturated. Examples of heterocycle include, but are not limited to, azetidine, pyrrolidine, piperidine, 2,8-diazaspiro[4.5]decane, piperazine, morpholine, and others.

"Heteroaryl" means an aromatic monocyclic or polycyclic system having from 5 to 11 carbon atoms, preferably from 5 to 10, of which one or more carbon atoms are substituted by one or more heteroatoms, such as nitrogen, sulfur or oxygen. Nitrogen atom of heterocycle could be oxidized to N-oxide. Heteroaryl may have one or more substituents which may be same or different structure.

Heteroaryl can be annelated with a cycloalkyl, heterocycle or aryl. Examples of heteroaryl include, but are not limited to, pyrrolyl, furanyl, thienyl, pyridyl, pyrazinyl, pyrimidinyl, pyridazinyl, isoxazolyl, isothiazolyl, tetrazolyl, oxazolyl, thiazolyl, pyrazolyl, furazanyl, triazolyl, 1,2,4-thiadiazolyl, quinoxalinyl, phthalazinyl, imidazo[1,2-a]pyridinyl, imidazo[2,1-b]thiazolyl, benzofurazanyl, indolyl, azaindolyl, benzimidazolyl, benzothiazenyl, quinolinyl, imidazolyl, pyrazolyl, thienopyridyl, quinazolinyl, naphthyridinyl, thienopyrimidinyl, pyrrolopyridinyl, imidazopyridyl, isoquinolinyl, benzoazaindolyl, 1,2,4-triazinyl, thienopyrrolyl, furopyrrolyl, and the like.

"Partially saturated" means a ring system including at least one double or triple bond. The term "partly saturated" relates to rings having many sites for saturation and does not include aryl and heteroaryl systems as they defined above.

The term "oxo" used in this document relates to the radical =O.

"Substituent" means a chemical radical attached to a scaffold (fragment).

"Solvate" is a molecular aggregate that consists of the compound of the present invention, or its pharmaceutically acceptable salt, with one or more solvent molecules. The solvent molecules are molecules of common pharmaceutical solvents, known to be safe for recipients, e.g. water, ethanol, ethylene glycol, etc. Other solvents, such as methanol, methyl-tert-butyl ether, ethyl acetate, methyl acetate, (R)-propylene glycol or (S)-propylene glycol, 1,4-butanediol, and the like, can be used to form intermediate solvates for obtaining preferable solvates.

"Hydrate" means a solvate with water as the solvent.

Solvates and/or hydrates preferably exist in crystalline form.

Terms "bond", "chemical bond", or "single bond" refer to a chemical bonding of two atoms or two moieties (i.e., groups, fragments) when the atoms joined by the bond are considered to be part of larger substructure.

The term "protecting group" refers to groups that are used to block the reactivity of functional groups, such as an amino group, carboxyl group or hydroxy group. Examples of protecting groups include, but are not limited to, tert-butyloxycarbonyl (Boc), benzyloxycarbonyl (Cbz), 2-(trimethylsilyl) ethoxy) methyl acetal (SEM), trialkylsilyl, alkyl (diaryl)silyl or alkyl.

The term "excipient" is used herein to describe any ingredient other than the compound(s) of the invention.

"Pharmaceutical composition" means a composition, comprising a compound of the invention and one or more pharmaceutically acceptable excipients. The excipient may be selected from the group consisting of pharmaceutically acceptable and pharmacologically compatible fillers, solvents, diluents, carriers, auxiliary, distributing and sensing agents, delivery agents, such as preservatives, stabilizers, filler, disintegrators, moisteners, emulsifiers, suspending agents, thickeners, sweeteners, flavouring agents, aromatizing agents, antibacterial agents, fungicides, lubricants, and prolonged delivery controllers, the choice and suitable proportions of which depend on the type and way of administration and dosage. Examples of suitable suspending agents are, without limitation, ethoxylated isostearyl alcohol, polyoxyethylene, sorbitol and sorbitol ether, microcrystalline cellulose, aluminum metahydroxide, bentonite, agar-agar and tragacant and their mixtures as well. Protection against action of microorganisms can be provided by various antibacterial and antifungal agents, such as, for example, parabens, chlorobutanole, sorbic acid, and similar compounds. Composition may also contain isotonic agents, such as, for example, sugars, sodium chloride, and similar compounds. Prolonged action of composition may be achieved by agents slowing down absorption of active ingredient, for example, aluminum monostearate and gelatine. Examples of suitable carriers, solvents, diluents and delivery agents include, but are not limited to, water, ethanol, polyalcohols and their mixtures, natural oils (such as olive oil) and organic esters (such as ethyl oleate) for injections. Examples of fillers are, but are not limited to, lactose, milk-sugar, sodium citrate, calcium carbonate, calcium phosphate and the like. Examples of disintegrators and distributors are, without limitation, starch, alginic acid and its salts, silicates and the like. Examples of suitable lubricants are, but are not limited to, magnesium stearate, sodium lauryl sulfate, talc and polyethylene glycol of high molecular weight. Pharmaceutical composition for peroral, sublingual, transdermal, intramuscular, intravenous, subcutaneous, local or rectal administration of active ingredient, alone or in combination with another active compound may be administered to human and animals in a standard administration form, in a mixture with traditional pharmaceutical carriers. Suitable standard administration forms include, but are not limited to, peroral forms such as tablets, gelatin capsules, pills, powders, granules, chewing-gums and peroral solutions or suspensions; sublingual and transbuccal administration forms; aerosols; implants; local, transdermal, subcutaneous, intramuscular, intravenous, intranasal or intraocular forms and rectal administration forms.

"Pharmaceutically acceptable salt" means relatively non-toxic both organic and inorganic salts of acids and bases disclosed in this invention. Salts of compounds provided herein can be obtained from inorganic or organic acids and bases. Examples of salts prepared in this manner include, but are not limited to, hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, methane sulphonates, malonates, salicylates, propionates, ethane sulphonates, benzene sulfonates, sulfamates and the like; sodium, potassium, ammonium, calcium, magnesium, iron, zinc, copper, manganese and aluminum salts, primary, secondary and tertiary amine salts, substituted amine salts, including naturally-occurring substituted amine salts, cyclic amine salts, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, ethylenediamine, glucosamine, methylglucamine, theobromine, purines, piperazine, piperidine, N-ethylpiperidine (Detailed description of such salts properties is given in: Berge S. M., et al., "Pharmaceutical Salts" J. Pharm. Sci. 1977, 66: 1-19). Aminoacids may be selected from lysine, ornithine and arginine.

"Medicament (medicine)"—is a compound (or a mixture of compounds as a pharmaceutical composition) in the form of tablets, capsules, injections, ointments and other ready forms intended for restoration, improvement or modification of physiological functions in humans and animals, and for treatment and prophylaxis of diseases, for diagnostics, anesthesia, contraception, cosmetology and others.

"Treat", "treating" and "treatment" refer to a method of alleviating or abrogating a biological disorder and/or at least one of its attendant symptoms. The term "alleviate" a disease, disorder or condition means reducing the severity and/or occurrence frequency of the symptoms of the disease, disorder, or condition. Further, references herein to "treatment" include references to curative, palliative and prophylactic treatment.

In one aspect, the subject of treatment, or patient, is a mammal, preferably a human subject. Said subject may be either male or female, of any age.

The term "disorder" means any condition that would benefit from treatment with the compound of the present invention. This means chronic and acute disorders or diseases including those pathological conditions that predispose the mammal to the disorder in question. Non-limiting examples of disorders to be treated herein include oncological diseases, in particular breast cancer, triple-negative breast cancer (TNBC), ovarian cancer, metastatic ovarian cancer, stomach cancer, metastatic stomach cancer, endometrial, salivary gland, lung, kidney or colon cancer; colorectal cancer, melanoma, metastatic melanoma, thyroid, pancreas, prostate or bladder cancer; haemato-oncological diseases, leucoses, acute myeloid leukemia and lymphoid malignancies, neuronal, glial, astrocytal, hypothalamic and other glandular, macrophagal, epithelial, stromal and blastocoelic disorders; inflammatory, angiogenic and immunologic disorders.

"Therapeutically effective amount" refers to that amount of the therapeutic agent being administered which will relieve to some extent one or more of the symptoms of the disease/disorder being treated.

In the present description and in the following claims, unless the context provides otherwise, the words "comprise," "have," "include," or variations such as "comprises," "comprising," "has," "having," "includes" or "including", and all grammatical variations thereof will be understood to imply the inclusion of a stated integer or group of integers but not the exclusion of any other integer or group of integers.

DETAILED DESCRIPTION OF THE INVENTION

In one embodiment, the present invention relates to the compound of formula I:

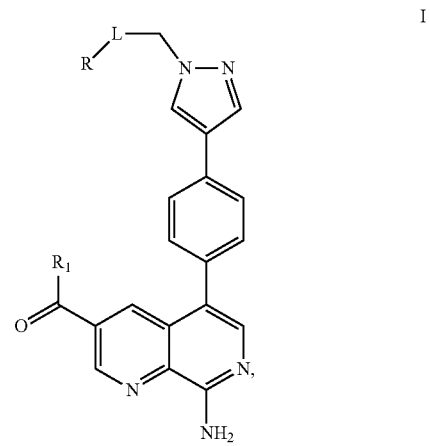

I or pharmaceutically acceptable salt or stereoisomer thereof, wherein L is —[$CH_2$]$_{0-3}$—, —[$CH_2$]$_{0-2}$—C(O)—, —C(O)—[$CH_2$]$_{0-2}$—;
R is —$NR^4R^5$, —$OR^6$;
$R^1$ is —$NR^2R^3$;
$R^2$ and $R^3$ is independently H; $C_{1-6}$ alkyl, unsubstituted or substituted by one or several substituents $R^7$; $C_{2-6}$ alkenyl, unsubstituted or substituted by one or several substituents $R^7$; $C_{2-6}$ alkynyl, unsubstituted or substituted by one or several substituents $R^7$; $C_{3-7}$ cycloalkyl, unsubstituted or substituted by one or several substituents $R^8$; $C_{3-7}$ cycloalkenyl, unsubstituted or substituted by one or several substituents $R^8$; 5-6 membered heterocyclyl with 1-2 heteroatoms, selected from N, O and/or S, unsubstituted or substituted by one or several substituents $R^9$; aryl, unsubstituted or substituted by one or several substituents $R^{10}$; heteroaryl with 1-4 heteroatoms, selected from N, O and/or S, unsubstituted or substituted by one or several substituents $R^{11}$, or
$R^2$ and $R^3$ together with the nitrogen atom they are attached to, form 4-7-membered heterocyclic ring with 1-3 heteroatoms, selected from N and/or O, wherein heterocyclic ring, formed by $R^2$ and $R^3$, could be unsubstituted or substituted by one or several substituents $R^9$;
$R^4$ and $R^5$ is independently H; $C_{1-6}$ alkyl, unsubstituted or substituted by one or several substituents $R^{12}$; $C_{2-6}$ alkenyl, unsubstituted or substituted by one or several substituents $R^{12}$; $C_{2-6}$ alkynyl, unsubstituted or substituted by one or several substituents $R^{12}$; $C_{3-7}$ cycloalkyl, unsubstituted or substituted by one or several substituents $R^{13}$; $C_{3-7}$ cycloalkenyl, unsubstituted or substituted by one or several substituents $R^{13}$; 5-6 membered heterocyclyl with 1-2 heteroatoms, selected from N, O and/or S, unsubstituted or substituted by one or several substituents $R^{14}$; aryl, unsubstituted or substituted by one or several substituents $R^{15}$; heteroaryl with 1-4 heteroatoms, selected from N, O and/or S, unsubstituted or substituted by one or several substituents $R^{16}$, or
$R^4$ and $R^5$ together with the nitrogen atom they are attached to, form 4-7-membered heterocyclic ring with 1-3 heteroatoms, selected from N and/or O, wherein heterocyclic ring, formed by $R^4$ and $R^5$, could be unsubstituted or substituted by one or several substituents $R^{14}$;

$R^6$ is H; $C_{1-6}$ alkyl, unsubstituted or substituted by one or several substituents $R^{17}$; each $R^7$ and $R^{12}$ is independently H, Hal, CN, $-OR^{18}$, $-NR^{19}R^{20}$, $-C(=O)R^{18}$, $-C(=O)NR^{19}R^{20}$, $-NR^{21}C(=O)R^{18}$; $-NR^{21}C(=O)NR^{19}R^{20}$; $-SO_2R^{22}$; $-SO_2NR^{23}R^{24}$, $C_{3-7}$ cycloalkyl, unsubstituted or substituted by one or several radicals, selected from $C_{1-6}$ alkyl, halogen;

each $R^9$ and $R^{14}$ is independently H, Hal, CN, $-OR^{18}$, $-NR^{19}R^{20}$, $-C(=O)R^{18}$, $-C(=O)NR^{19}R^{20}$, $-NR^{21}C(=O)R^{18}$; $-NR^{21}C(=O)NR^{19}R^{20}$; $-SO_2R^{22}$; $-SO_2NR^{23}R^{24}$, oxo group, $C_{1-6}$ alkyl, unsubstituted or substituted by one or several halogens; $C_{3-7}$ cycloalkyl, unsubstituted or substituted by one or several radicals, selected from $C_{1-6}$ alkyl, halogen;

each $R^8$, $R^{10}$, $R^{11}$, $R^{13}$, $R^{15}$ and $R^{16}$, is independently H, Hal, CN, $-OR^{18}$, $-NR^{19}R^{20}$, $-C(=O)R^{18}$, $-C(=O)NR^{19}R^{20}$, $-NR^{21}C(=O)R^{18}$; $-NR^{21}C(=O)NR^{19}R^{20}$; $-SO_2R^{22}$; $-SO_2NR^{23}R^{24}$, $C_1$-$C_6$ alkyl, unsubstituted or substituted by one or several halogens; $C_{3-7}$ cycloalkyl, unsubstituted or substituted by one or several radicals, selected from $C_{1-6}$ alkyl, halogen;

each $R^{17}$, $R^{18}$, $R^{19}$, $R^{20}$ and $R^{21}$ is independently H, $C_1$-$C_6$ alkyl, unsubstituted or substituted by one or several halogens; $C_2$-$C_6$ alkenyl, $C_2$-$C_6$ alkynyl, $C_3$-$C_7$ cycloalkyl, unsubstituted or substituted by one or several radicals, selected from $C_{1-6}$ alkyl, halogen; or $R^{19}$ and $R^{20}$ together with the nitrogen atom they are attached to, form 4-7-membered heterocyclic ring with 1-3 heteroatoms, selected from N and/or O, wherein the heterocyclic ring, formed by $R^{19}$ and $R^{20}$, could be unsubstituted or substituted by 1 or 2 substituents, selected from oxo group; Hal; OH; $NH_2$; CN; $C_{1-6}$ alkyl, unsubstituted or substituted by one or several halogens; $C_{1-6}$ alkoxy; $C_{1-6}$ alkylamino.

In another one embodiment, the present invention relates to the compound of formula I, wherein L is $-C(O)-$, $-CH_2-$.

In another one embodiment, the present invention relates to the compound of formula I, wherein $R^1$ is $-NR^2R^3$, wherein $R^2$ and $R^3$ is independently H; $C_{1-6}$ alkyl, unsubstituted or substituted by one or several substituents $R^7$; $C_{2-6}$ alkenyl, unsubstituted or substituted by one or several substituents $R^7$; $C_{2-6}$ alkynyl, unsubstituted or substituted by one or several substituents $R^7$; $C_{3-7}$ cycloalkyl, unsubstituted or substituted by one or several substituents $R^8$; $C_{3-7}$ cycloalkenyl, unsubstituted or substituted by one or several substituents $R^8$; 5-6 membered heterocyclyl with 1-2 heteroatoms, selected from N, O and/or S, unsubstituted or substituted by one or several substituents $R^9$; aryl, unsubstituted or substituted by one or several substituents $R^{10}$; heteroaryl with 1-4 heteroatoms, selected from N, O and/or S, unsubstituted or substituted by one or several substituents $R^{11}$, $R^7$, $R^8$, $R^9$, $R^{10}$, $R^{11}$ have the above meanings; or wherein $R^1$ is:

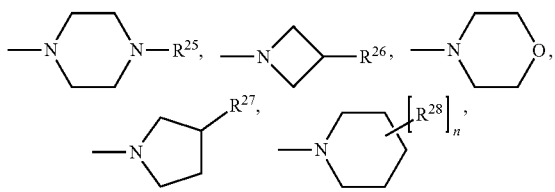

$R^{25}$ is H, $C_{1-6}$ alkyl;
$R^{26}$, $R^{27}$, $R^{28}$ are H, CN, OH, $C_{1-6}$ alkyl, $C_{1-4}$ alkoxy;
n is 0, 1, 2, 3.

In another one embodiment, the present invention relates to the compound of formula I, wherein R is $-NR^4R^5$, $-OR^6$;

each $R^4$ and $R^5$ is independently H; $C_{1-6}$ alkyl, unsubstituted or substituted by one or several substituents $R^{12}$; $C_{2-6}$ alkenyl, unsubstituted or substituted by one or several substituents $R^{12}$; $C_{2-6}$ alkynyl, unsubstituted or substituted by one or several substituents $R^{12}$; $C_{3-7}$ cycloalkyl, unsubstituted or substituted by one or several substituents $R^{13}$; $C_{3-7}$ cycloalkenyl, unsubstituted or substituted by one or several substituents $R^{13}$; 5-6 membered heterocyclyl with 1-2 heteroatoms, selected from N, O and/or S, unsubstituted or substituted by one or several substituents $R^{14}$; aryl, unsubstituted or substituted by one or several substituents $R^{15}$; heteroaryl with 1-4 heteroatoms, selected from N, O and/or S, unsubstituted or substituted by one or several substituents $R^{16}$;

$R^{12}$, $R^{13}$, $R^{14}$, $R^{15}$, $R^{16}$ have the above meanings; or wherein $R^4$ and $R^5$ together with the nitrogen atom they are attached to, form 4-7-membered heterocyclic ring with 1-3 heteroatoms, selected from N and/or O, wherein heterocyclic ring, formed by $R^4$ and $R^5$, could be unsubstituted or substituted by one or several substituents $R^{14}$, wherein the 4-7-membered heterocyclic ring is

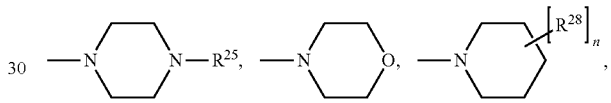

$R^{25}$ is H, $C_{1-6}$ alkyl;
$R^{28}$ are H, CN, OH, $C_{1-6}$ alkyl, $C_{1-4}$ alkoxy;
n is 0, 1, 2, 3;
$R^6$ is $C_{1-6}$ alkyl, unsubstituted or substituted by one or several substituents $R^{17}$;
$R^{17}$ have the above meanings.

In another one embodiment, the present invention relates to the compound of formula I, wherein $R^1$ is $-NR^2R^3$, wherein $R^2$ and $R^3$ is independently H; $C_{1-6}$ alkyl, unsubstituted or substituted by one or several substituents $R^7$; $C_{3-7}$ cycloalkyl, unsubstituted or substituted by one or several substituents $R^8$; 5-6 membered heterocyclyl with 1-2 heteroatoms, selected from N, O and/or S, unsubstituted or substituted by one or several substituents $R^9$; aryl, unsubstituted or substituted by one or several substituents $R^{10}$; heteroaryl with 1-4 heteroatoms, selected from N, O and/or S, unsubstituted or substituted by one or several substituents $R^{11}$;

each $R^7$ and $R^9$ is independently H, Hal, CN, $-OR^{18}$, $-NR^{19}R^{20}$, $-C(=O)R^{18}$, $-C(=O)NR^{19}R^{20}$;

each $R^8$, $R^{10}$ and $R^{11}$ is independently H, Hal, CN, $-OR^{18}$, $-NR^{19}R^{20}$, $-C(=O)R^{18}$, $-C(=O)NR^{19}R^{20}$, $C_1$-$C_6$ alkyl, unsubstituted or substituted by one or several halogens; each $R^{18}$, $R^{19}$ and $R^{20}$ is independently H, $C_1$-$C_6$ alkyl, unsubstituted or substituted by one or several halogens; $C_3$-$C_7$ cycloalkyl, unsubstituted or substituted by one or several radicals, selected from $C_{1-6}$ alkyl, halogen; or wherein $R^1$ is:

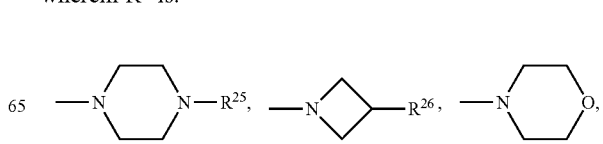

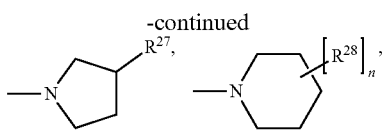 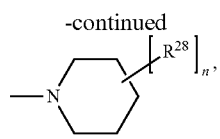

$R^{25}$ is H, $C_{1-6}$ alkyl;
$R^{26}$, $R^{27}$, $R^{28}$ are H, CN, OH, $C_{1-4}$ alkoxy;
n is 0, 1, 2, 3.

In another one embodiment, the present invention relates to the compound of formula I, wherein R is —NR⁴R⁵, —OR⁶;
each $R^4$ and $R^5$ is independently H; $C_{1-6}$ alkyl, unsubstituted or substituted by one or several substituents $R^{12}$; $C_{3-7}$ cycloalkyl, unsubstituted or substituted by one or several substituents $R^{13}$; 5-6 membered heterocyclyl with 1-2 heteroatoms, selected from N, O and/or S, unsubstituted or substituted by one or several substituents $R^{14}$; aryl, unsubstituted or substituted by one or several substituents $R^{15}$; heteroaryl with 1-4 heteroatoms, selected from N, O and/or S, unsubstituted or substituted by one or several substituents $R^{16}$;
each $R^{12}$ and $R^{14}$ is independently H, Hal, CN, —OR¹⁸, —NR¹⁹R²⁰, —C(═O)NR¹⁸, —C(═O)NR¹⁹R²⁰;
each $R^{13}$, $R^{15}$ and $R^{16}$ is independently H, Hal, CN, —OR¹⁸, —NR¹⁹R²⁰, —C(═O)NR¹⁸, —C(═O)NR¹⁹R²⁰, $C_1$-$C_6$ alkyl, unsubstituted or substituted by one or several halogens; each $R^{18}$, $R^{19}$ and $R^{20}$ is independently H, $C_1$-$C_6$ alkyl, unsubstituted or substituted by one or several halogens; $C_3$-$C_7$ cycloalkyl, unsubstituted or substituted by one or several radicals, selected from $C_{1-6}$ alkyl, halogen; or
wherein $R^4$ and $R^5$ together with the nitrogen atom they are attached to, form 4-7-membered heterocyclic ring with 1-3 heteroatoms, selected from N and/or O, wherein heterocyclic ring, formed by $R^4$ and $R^5$, could be unsubstituted or substituted by one or several substituents $R^{14}$,
wherein the 4-7-membered heterocyclic ring is

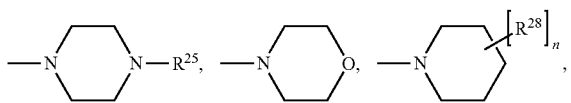

$R^{25}$ is H, $C_{1-6}$ alkyl;
$R^{28}$ are H, CN, OH, $C_{1-4}$ alkoxy;
n is 0, 1, 2, 3;
$R^6$ is $C_{1-6}$ alkyl, unsubstituted or substituted by one or several halogens.

In another one embodiment, the present invention relates to the compound of formula I, wherein $R^1$ is —NR²R³,
wherein $R^2$ and $R^3$ is independently H; $C_{1-6}$ alkyl, unsubstituted or substituted by one or several substituents $R^7$;
$R^7$ is H, Hal, —OR¹⁸, $C_{3-7}$ cycloalkyl, unsubstituted or substituted by one or several radicals, selected from $C_{1-6}$ alkyl, halogen;
$R^{18}$ is H, $C_1$-$C_6$ alkyl; or
wherein $R^1$ is:

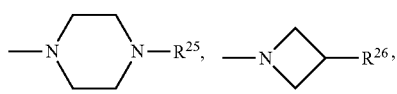

$R^{25}$ is H, $C_{1-6}$ alkyl;
$R^{26}$ and $R^{28}$ are H, OH, $C_{1-6}$ alkyl, $C_{1-4}$ alkoxy;
n is 0, 1.

In another one embodiment, the present invention relates to the compound of formula I, wherein R is —NR⁴R⁵, —OR⁶;
each $R^4$ and $R^5$ is independently H; $C_{1-6}$ alkyl, unsubstituted or substituted by one or several substituents $R^{12}$; or
$R^6$ is $C_{1-6}$ alkyl, unsubstituted or substituted by one or several halogens;
$R^{12}$ is H, Hal, —OR¹⁸, $C_{3-7}$ cycloalkyl, unsubstituted or substituted by one or several radicals, selected from $C_{1-6}$ alkyl, halogen;
each $R^{18}$ is independently H, $C_1$-$C_6$ alkyl, unsubstituted or substituted by one or several halogens;
wherein R is:

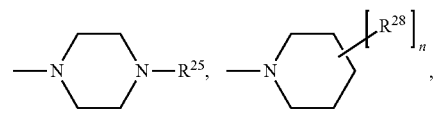

$R^{25}$ is H, $C_{1-6}$ alkyl;
$R^{28}$ are H, OH, $C_{1-6}$ alkyl, $C_{1-4}$ alkoxy;
n is 0, 1.

In another one embodiment, the present invention relates to the compound of formula I, wherein $R^1$ is:

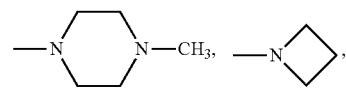

—NR²R³,
each $R^2$ and $R^3$ is independently H; $C_{1-6}$ alkyl, unsubstituted or substituted by Hal, —OR¹⁸, $C_{3-7}$ cycloalkyl; $C_{3-7}$ cycloalkyl;
$R^{18}$ is H, $C_{1-6}$ alkyl.

In another one embodiment, the present invention relates to the compound of formula I, wherein $R^1$ is:

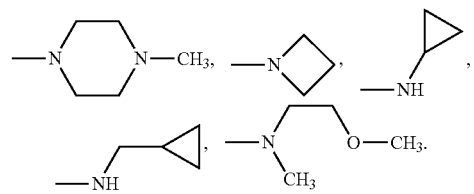

In another one embodiment, the present invention relates to the compound of formula I, wherein R is:

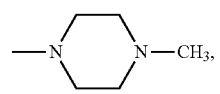

—NR⁴R⁵, —O—R⁶; wherein
each R⁴ and R⁵ is independently H; $C_{1-6}$ alkyl;
R⁶ is $C_{1-6}$ alkyl.

In another one embodiment, the present invention relates to the compound of formula I, wherein R is:

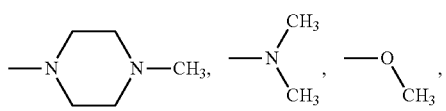

In another one embodiment, the present invention relates to the compound of formula I, wherein -L-R is:

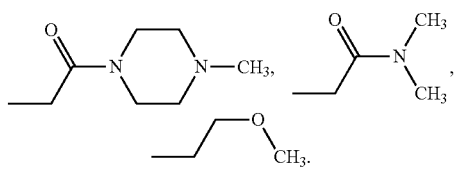

Compounds, described in the present invention, may be formed as, and/or used as, pharmaceutically acceptable salts. The type of pharmaceutical acceptable salts, include, but are not limited to: acid salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-3-hydroxy-2-ene-1-carboxylic acid, 3-phenylpropionic acid, trimethylacetic acid, tert-butylacetic acid, lauryl sulfuric acid, gluconic acid, glutamic acid, hydroxynaphthoic acid, salicylic acid, stearic acid, muconic acid, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following methods: filtration, precipitation with a non-solvent followed by filtration, evaporation of the solvent, or, in the case of aqueous solutions, lyophilization. It should be understood that a reference to a pharmaceutically acceptable salt includes the solvent addition forms or crystal forms thereof, particularly solvates or polymorphs. Solvates contain either stoichiometric or non-stoichiometric amounts of a solvent and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered as equivalent to the unsolvated forms for the purposes of the compounds and methods provided herein.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause one crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address to analysis of thermo chemical degradation or thermo physical processes including, but not limited to, polymorphic transitions, and such methods are used to analyze the relationships between polymorphic forms, to determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), Thermogravimetric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

In another embodiment of the present invention relates to the compounds selected from the group including:

| No. | Formula | Name |
|---|---|---|
| 3.43 | | 8-Amino-N-(cyclopropylmethyl)-5-(4-(1-(2-(dimethylamino)-2-oxoethyl)-1H-pyrazole-4-yl)phenyl)-1,7-naphthyridine-3-carboxamide |
| 3.44 | | 8-amino-N-(cyclopropylmethyl)-5-(4-(1-(2-(4-methylpiperazin-1-yl)-2-oxoethyl)-1H-pyrazole-4-yl)phenyl)-1,7-naphthyridine-3-carboxamide |
| 3.45 | | 8-amino-N-(cyclopropylmethyl)-5-(4-(1-(2-methoxyethyl)-1H-pyrazole-4-yl)phenyl)-1,7-naphthyridine-3-carboxamide |

-continued
| No. | Formula | Name |
|---|---|---|
| 3.46 | 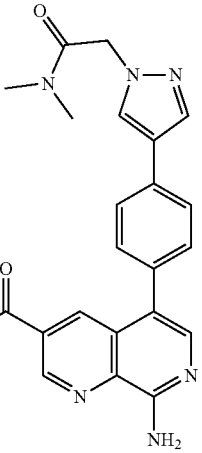 | 8-amino-N-cyclopropyl-5-(4-(1-(2-(dimethylamino)-2-oxoethyl)-1H-pyrazole-4-yl)phenyl)-1,7-naphthyridine-3-carboxamide |
| 3.47 | 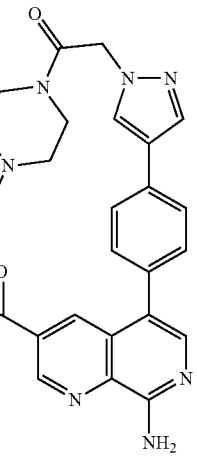 | 8-amino-N-cyclopropyl-5-(4-(1-(2-(4-methylpiperazin-1-yl)-2-oxoethyl)-1H-pyrazole-4-yl)phenyl)-1,7-naphthyridine-3-carboxamide |
| 3.48 | 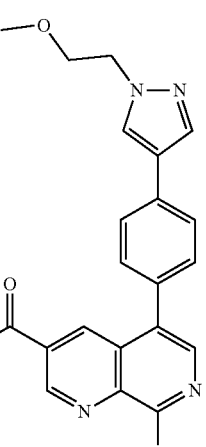 | 8-amino-N-cyclopropyl-5-(4-(1-(2-(2-methoxyethyl)-1H-pyrazole-4-yl)phenyl)-1,7-naphthyridine-3-carboxamide |

-continued
| No. | Formula | Name |
|---|---|---|
| 3.49 | 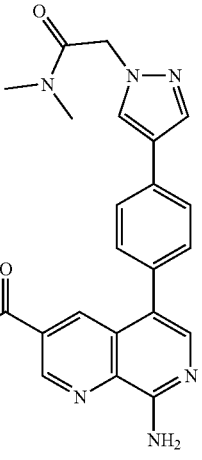 | 2-(4-(4-(8-amino-3-(4-methylpiperazine-1-carbonyl)-1,7-naphthyridine-5-yl)phenyl)-1H-pyrazole-1-yl)-N,N-dimethylacetamide |
| 3.49 × 2HCl | 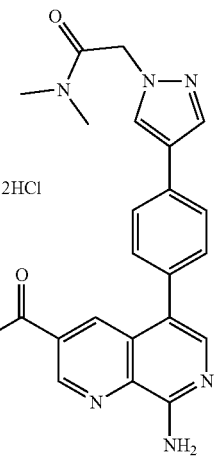 | 2-(4-(4-(8-amino-3-(4-methylpiperazine-1-carbonyl)-1,7-naphthyridine-5-yl)phenyl)-1H-pyrazole-1-yl)-N,N-dimethylacetamide dihydrochloride |
| 3.50 | 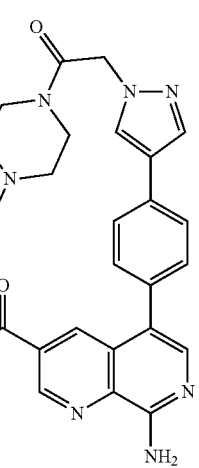 | 2-(4-(4-(8-amino-3-(4-methylpiperazine-1-carbonyl)-1,7-naphthyridine-5-yl)phenyl)-1H-pyrazole-1-yl)-1-(4-methylpiperazine-1yl)ethan-1-one |

-continued

| No. | Formula | Name |
|---|---|---|
| 3.51 | | (8-amino-5-(4-(1-(2-methoxyethyl)-1H-pyrazole-4-yl)phenyl)-1,7-naphthyridin-3-yl)(4-methylpiperazine-1-yl)methanone |
| 3.52 | | 2-(4-(4-(8-amino-3-(azetidine-1-carbonyl)-1,7-naphthyridine-5-yl)phenyl)-1H-pyrazole-1-yl)-N,N-dimethylacetamide |
| 3.53 | | 2-(4-(4-(8-amino-3-(azetidine-1-carbonyl)-1,7-naphthyridine-5-yl)phenyl)-1H-pyrazole-1-yl)-1-(4-methylpiperazine-1-yl)ethan-1-one |

| No. | Formula | Name |
| --- | --- | --- |
| 3.54 | | (8-amino-5-(4-(1-(2-methoxyethyl)-1H-pyrazole-4-yl)phenyl)-1,7-naphthyridin-3-yl) (azetidin-1-yl)methanone |
| 3.55 | | 8-amino-5-(4-(1-(2-(dimethylamino)-2-oxoethyl)-1H-pyrazole-4-yl) phenyl-N-(2-methoxyethyl)-N-methyl-1,7-naphthyridine-3-carboxamide |
| 3.56 | | 8-amino-N-(2-methoxyethyl)-N-methyl-5-(4-(1-(2-(4-methylpiperazine-1-yl)-2-oxoethyl)-1H-pyrazole-4-yl)phenyl)-1,7-naphthyridine-3-carboxamide |

| No. | Formula | Name |
| --- | --- | --- |
| 3.57 | | 8-amino-N-(2-methoxyethyl)-5-(4-(1-(2-methoxyethyl)-1H-pyrazole-4-yl)phenyl)-N-methyl-1,7-naphthyridine-3-carboxamide |

The present invention also relates to a method for inhibiting of biological activity of cyclin-dependent protein kinases CDK8/19 in a subject, comprising contacting the cyclin-dependent protein kinases CDK8/19 with the compound described herein.

In one embodiment, the present invention relates to a pharmaceutical composition that comprises a therapeutically effective amount of at least one of the compounds described herein, or pharmaceutically acceptable salt, solvate thereof, and one or more pharmaceutically acceptable excipients. In another one embodiment, the pharmaceutical composition of the present invention is intended to treat or prevent a disease or disorder mediated by the activation of cyclin-dependent protein kinases CDK8/19. In another one embodiment, the present invention relates to a pharmaceutical composition for the prevention or treatment of a disease or disorder mediated by the activation of cyclin-dependent protein kinases CDK8/19, wherein the disease or disorder mediated by the activation of cyclin-dependent protein kinases CDK8/19 is an oncological or haemato-oncological. In another one embodiment, the pharmaceutical composition of the present invention is intended to treat or prevent colorectal cancer, melanoma, breast cancer, triple-negative breast cancer (TNBC), prostate cancer, metastatic ovarian cancer, metastatic stomach cancer, leucosis, acute myeloid leukemia, pancreatic cancer.

The pharmaceutical composition of the present invention comprises, for example, from about 10% to about 100% of active ingredients, preferably from about 20% to about 60% of active ingredients. It is to be understood that each dosage unit may not comprise an effective amount of an active ingredient or ingredients, because the sufficient effective amount can be achieved by multiple dosing.

A typical composition is prepared by mixing the compound described herein with one or several excipients. Examples of excipients include, but are not limited to, diluents, carriers, fillers. Suitable carriers, diluents and fillers are well known to those skilled in the art and include, but are not limited to, materials such as carbohydrates, waxes, water soluble and/or swellable polymers, hydrophilic or hydrophobic materials, gelatin, oils, solvents, water, and the like. The particular carrier, diluent or filler used will depend upon the means and purpose for which compound of the present invention is being applied. Solvents are generally selected based on solvents recognized by persons skilled in the art as safe to be administered to a mammal. In general, safe solvents are non-toxic aqueous solvents such as water and other non-toxic solvents that are soluble or miscible in water. Suitable aqueous solvents include water as the main component, ethanol, propylene glycol, polyethylene glycols (e.g., PEG400, PEG300), etc. and mixtures thereof. The compositions may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., compound of the invention or pharmaceutical composition thereof) or aid in the manufacturing of the pharmaceutical product (i.e., medicament).

The pharmaceutical compositions also include solvates and hydrates of compounds of the present invention, or stabilized form of the compound (e.g., complex with a cyclodextrin derivative or other known complexation agent).

The pharmaceutical compositions of the invention may be formulated for an oral route administration. Oral administration may involve swallowing the medicine, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; granules; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The pharmaceutical compositions of the invention could be used for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Intratumoral delivery, e.g. intratumoral injection, may also be advantageous. Regional perfusion is also contemplated.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like.

Formulations may be formulated to be immediate and/or modified release. Modified release formulations include delayed-, sustained-, pulsed-, controlled-, targeted and programmed release.

In one embodiment, the present invention relates to the method for treating a disease or disorder mediated by the activation of cyclin-dependent protein kinases CDK8/19 that comprises the step of administering a therapeutically effective amount of the compound of the present invention, or pharmaceutically acceptable salt thereof, or the pharmaceutical composition of the present invention in a subject in need thereof.

In another one embodiment, the present invention relates to the method for treating a disease or disorder mediated by the activation of cyclin-dependent protein kinases CDK8/19, which is either oncological or haemato-oncological, that comprises the step of administering a therapeutically effective amount of any compound described herein, or a pharmaceutical composition of the present invention to a subject in need of such treatment.

In another one embodiment, the present invention relates to the described above method wherein oncological and haemato-oncological disease is selected from the group comprising colorectal cancer, melanoma, breast cancer, triple-negative breast cancer (TNBC), prostate cancer, metastatic ovarian cancer, metastatic stomach cancer, leucosis, acute myeloid leukemia, pancreatic cancer.

It is understood that the compounds of the invention may be used in methods for treating, as described above, in treatment, as described above, and/or in the manufacture of a medicament for the therapeutic applications.

As used herein, the terms "co-administration", "co-administered" and "in combination with" referring to the compounds with one or more other therapeutic agents, is intended to mean, and does refer to and include the following:

simultaneous administration of such combination of compound of the invention and therapeutic agent(s) to a patient in need of treatment, when such components are formulated together into a single dosage form which releases said components at substantially the same time to said patient, substantially simultaneous administration of such combination of compound of the invention and therapeutic agent(s) to a patient in need of treatment, when such components are formulated apart from each other into separate dosage forms which are taken at substantially the same time by said patient, whereupon said components are released at substantially the same time to said patient, sequential administration of such combination of compound of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound of the invention and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

As well known to those skilled in the art, therapeutically effective dosages may vary when the drugs are used in combination treatment. Methods for experimentally determining therapeutically effective dosages of drugs and other agents for use in combination treatment regimens are described in the literature. For example, the use of metronomic dosing, i.e., providing more frequent, lower doses in order to minimize toxic side effects, has been described in the literature. Combination treatment further includes periodic treatments that start and stop at various times to assist with the clinical management of the patient. For combination therapies described herein, dosages of the co-administered compounds will of course vary depending on the type of co-drug employed, on the specific drug employed, on the condition or disorder being treated and so forth.

In addition, compounds described herein may also be used in combination with procedures that may provide additional or synergistic benefit to the subject. By way of example only, subjects are expected to find therapeutic and/or prophylactic benefit in the methods described herein, wherein pharmaceutical composition of the present invention and/or combinations with other therapeutics are combined with genetic testing to determine whether that individual is a carrier of a mutant gene that is known to be correlated with certain diseases or conditions.

Compounds which are inhibitors of CDK8/19 can be used in the described above treatment methods in the form of monotherapy, or in combination with surgery, or radiation therapy, or drug therapy.

Such drug therapy may comprise administration of one or more of the anti-cancer agents. Examples of anti-cancer agents include, but are not limited to, any of the following agents: alkylating agents, alkyl sulfonates, nitrosoureas or triazenes; antimetabolites hormones and antagonists; platinum compounds; anticancer antibiotics; topoisomerase inhibitors.

Examples of antimetabolites include, but are not limited to, folic acid analog (such as methotrexate, trimetrexate, pemetrexed, pralatrexate, raltitrexed, calcium levofolinate) or pyrimidine analogs (such as cytarabine, tegafur, fluorouracil, capecitabine, floxuridine, azacitidine, enocitabine, carmofur, gemcitabine, sapacitabine, elacytarabine, doxifiuridine), or purine analogs (such as mercaptopurine, thioguanine, pentostatin, fludarabine, cladribine, nelarabine, azathioprine, clofarabine), or asparaginase.

Examples of alkylating agents include, but are not limited to, mechloretamine, cyclophosphamide, chlorambucil, melphalan, bendamustine, hexamethylmelamine, thiotepa, busulfan, carmustine, lomustine, laromustine, semustine, streptozocin, dacarbazine, ifosfamide, improsulfan, mitobronitol, mitolactol, nimustine, ranimustine, temozolomide, treosulfan, carboquone, apaziquone, fotemustine, altretamine, glufosfamide, pipobroman, trofosfamide, uramustine, evofosfamide, VAL-083.

Examples of hormones and antagonists include, but are not limited to, prednisone, prednisolone, hydroxyprogesterone caproate, megestrol acetate, medroxyprogesterone acetate, diethylstilbestrol, estradiol, tamoxifen, testosterone propionate, fluoxymesterone, flutamide, leuprolide, abarelix, abiraterone, bicalutamide, buserelin, calusterone, chlorotrianisene, degarelix, dexamethasone, fluocortolone, fulvestrant, goserelin, histrelin, leuprorelin, mitotane, nafarelin, nandrolone, nilutamide, octreotide, raloxifene, thyrotropin alfa, toremifene, triptorelin, diethylstilbestrol; acolbifene, danazol, deslorelin, epitiostanol, orteronel, enzalutamide, aminoglutethimide, anastrozole, exemestane, fadrozole, letrozole, testolactone; formestane.

Examples of platinum compounds include, but are not limited to, cisplatin, carboplatin, oxaliplatin, eptaplatin, miriplatine hydrate, lobaplatin, nedaplatin, picoplatin, satraplatin.

Examples of antitumor antibiotics include, but are not limited to, doxorubicin, daunurobicin, idarubicin, carubicin, valrubicin, zorubicin, aclarubicin, pirarubicin, nemorubicin, amrubicin, epirubicin, bleomycin, dactinomycin, plicamycin, peplomycin, mitomycin C, zinostatin, streptozocin.

Examples of topoisomerase inhibitors include, but are not limited to, irinotecan, topotecan, belotecan, teniposide, etoposide, voreloxin, amonafide.

Examples of anti-cancer agents include, but are not limited to, any of the following agents: microtubule-directed drugs, such as taxanes (e. g., paclitaxel, docetaxel, cabazitaxel, tezetaxel), vinca alkaloids (e. g., vinorelbine, vinblastine, vincristine, vindesine, vinflunine); mitogen-activated protein kinase signaling inhibitors (e. g., U0126, PD98059, PD184352, PD0325901, ARRY-142886, SB239063, SP600125, BAY 43-9006, wortmannin or LY294002); mTOR inhibitors (e. g., sirolimus, temsirolimus, everolimus, ridaforolimus); antibodies (e. g., rituximab, trastuzumab, alemtuzumab, besilesomab, cetuximab, denosumab, ipilimumab, bevacizumab, pertuzumab, nivolumab, ofatumumab, panitumumab, tositumomab, katumaksomab, elotuzumab, epratuzumab, farletuzumab, mogamulizumab, necitumumab, nimotuzumab, obinutuzumab, okaratuzumab, oregovomab, ramucirumab, rilotumumab, siltuximab, tocilizumab, zalutumumab, zanolimumab, matuzumab, dalotuzumab, onartuzumab, racotumomab, tabalumab, EDM-525797); kinase inhibitors (fostamatinib, entospletenib, erlotinib, imatinib, lapatinib, nilotinib, pazopanib, vemurafenib, gefitinib, crizotinib, dasatinib, regorafenib, ruxolitinib, sorafenib, sunitinib, vandetanib, bosutinib, axitinib, afatinib, alisertib, dabrafenib, dacomitinib, dinaciklib, dovitinib, nintedanib, lenvatinib, linifanib, linsitinib, masitinib, motesanib, neratinib, orantinib, ponatinib, radotinib, tipifarnib, tivantinib, tivozanib, trametinib, apatinib, ibrutinib, acalabrutinib, cobimetinib, fedratinib, brivanib alaninate, cediranib, cabozantinib, icotinib, cipatinib, rigosertib, pimasertib, buparlisib, idelalisib, midostaurin, perifosine, XL-647); photosensitizers (e. g., talaporfin, temoporfin, porfimer sodium); cytokines (e. g., aldesleukin, interferon alfa, interferon alfa-2a, interferon alfa-2b, celmoleukin, tasonermin, recombinant interleukin-2, oprelvekin, recombinant interferon beta-1a); vaccines (e. g., picibanil, sipuleucel-T, vitespen, emepepimut-S, oncoVAX, rindopepimut, troVAX, MGN-1601, MGN-1703); bisanthrene, decitabine, mitoxantrone, procarbazine, trabectedin, amsacrine, brostallicin, miltefosine, romidepsin, plitidepsin, eribulin, Ixabepilone, fosbretabulin, denileukin diftitox, ibritumomab tiuxetan, prednimustine, trastuzumab emtansine, estramustine, gemtuzumab ozogamicin, aflibercept, oportuzumab monatox, cintredekin besudotox, edotreotide, inotuzumab ozogamicin, naptumomab estafenatox, vintafolide, brentuximab vedotin, bortezomib, Ixazomib, carfilzomib, lenalidomide, thalidomide, pomalidomide, zoledronic acid, ibandronic acid, pamidronic acid, alitretinoin, tretinoin, peretinoin, bexarotene, tamibarotene, imiquimod, lentinan, mifamurtide, romurtide, pegaspargase, pentostatin, endostatin, sizofiran, vismodegib, vorinostat, entinostat, panobinostat, celecoxib, cilengitide, ethanidazole, ganetespib, idronoksil, Iniparib, lonidamine, nimorazole, procodazole, tasquinimod, telotrystat, belinostat, thymalfasin, tirapazamine, tosedostat, trabedersen, ubenimex, valspodar, gendicine, reolysin, retaspimycin, trebananib, virulizin.

In one embodiment, the present invention relates to use of the compound described herein or pharmaceutically acceptable salt thereof, or a pharmaceutical composition of the present invention in the treatment of a disease or disorder mediated by the activation of cyclin-dependent protein kinases CDK8/19 in a subject in need thereof.

In another one embodiment, the present invention relates to the use of the compound described herein or pharmaceutically acceptable salt thereof, or the pharmaceutical composition of the present invention in the treatment of a disease or disorder mediated by the activation of cyclin-dependent protein kinases CDK8/19 in a subject in need thereof, which is either oncological or haemato-oncological.

In another one embodiment, the present invention relates to the use of the compound described above or pharmaceutically acceptable salt thereof, or the pharmaceutical composition of the present invention in the treatment of an oncological or haemato-oncological disease selected from the group comprising colorectal cancer, melanoma, metastatic melanoma, breast cancer, triple-negative breast cancer (TNBC), prostate cancer, metastatic ovarian cancer, metastatic stomach cancer, leucosis, acute myeloid leukemia, pancreatic cancer in a subject in need of such treatment. In all of these embodiments, the subject may be human.

The compounds of the invention will be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the compounds are being administered as a stand-alone treatment or in combination with one or more additional treatments.

Dosage regimens may be adjusted to provide the optimum desired response. For example, a single dose may be administered, several divided doses may be administered over time or the dose may be proportionally reduced or increased as indicated by the exigencies of the therapeutic situation. It is especially advantageous to formulate oral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier.

It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of this invention may be based on a variety of factors, including the type of disease, the age, weight, sex, medical condition of the patient, the severity of the condition, the route of administration, and the particular compound employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the person skilled in the art. Determining appropriate dosages and regimens are well-known in the relevant art and would be understood to be encompassed by the person skilled in the art once provided the teachings disclosed herein.

Generally, standard daily dosage for an adult human is in the range from 0.02 mg to 5000 mg per day or from about 1 mg to about 1500 mg per day.

Once improvement of the patient's conditions has occurred, a maintenance dose is administered, if necessary. Subsequently, the dosage or the frequency of administration, or both, can be reduced, as a function of the symptoms, to a level at which the improved disease or disorder is retained. Patients may be required periodic treatment on a long-term basis upon any relapse of symptoms.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disorder or condition to be treated, the method of administration, the requirements of the individual subject, the severity of the disorder or condition being treated, and the judgment of the physician.

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended embodiments.

In order that this invention may be better understood, the following examples are set forth. These examples are for purposes of illustration only and are not to be construed as limiting the scope of the invention in any manner.

Abbreviations in this description, including those shown in illustrative schemes and the examples described below are well-known for an average person skilled in the art. Some of the abbreviations are as follows:
dimethyl sulfoxide—DMSO
(±)-2.2'-bis(diphenylphosphino)-1.1'-dinaphthalene—BINAP
N-(3-dimethylaminopropyl)-N'-ethylcarbodiimide hydrochloride—EDC×HCl
1-hydroxybenzotriazole hydrate—HOBt
N,N-dimethylformamide—DMF
tetrakis(triphenylphosphine)palladium(0)—Pd(PPh$_3$)$_4$
tetrahydrofuran—THF
Tetramethylethylenediamine—TMEDA
Sodium bis(trimethylsilyl)amide—NaHMDS
[1,1'-Bis(diphenylphosphino)ferrocene]dichloropalladium (II), complex with dichloromethane—PddppfCl$_2$×DCM.
4-dimethylaminopyridine—DMAP

EXAMPLES

Example 1. Method of Preparation of Compound 1.0

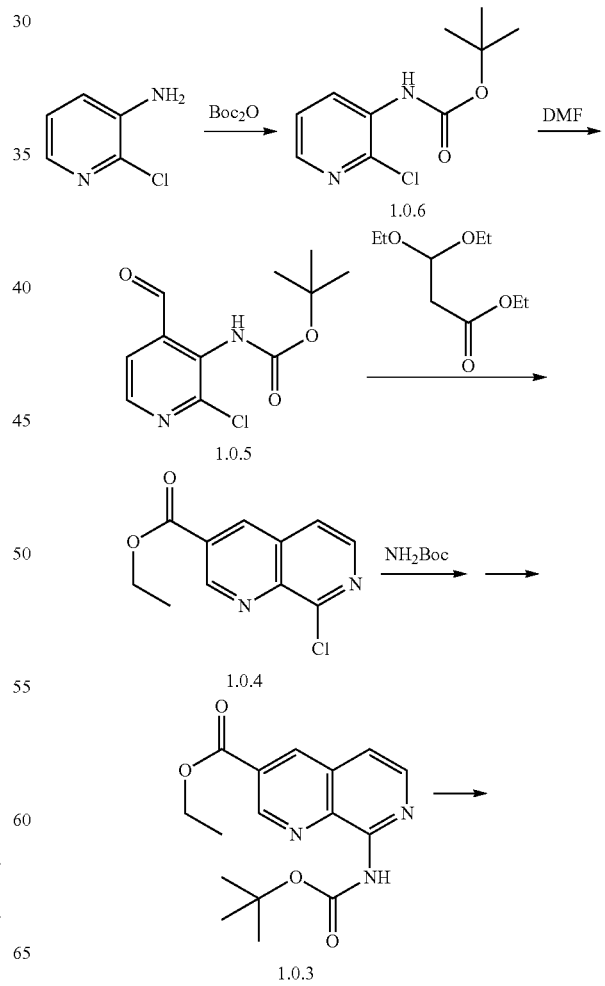

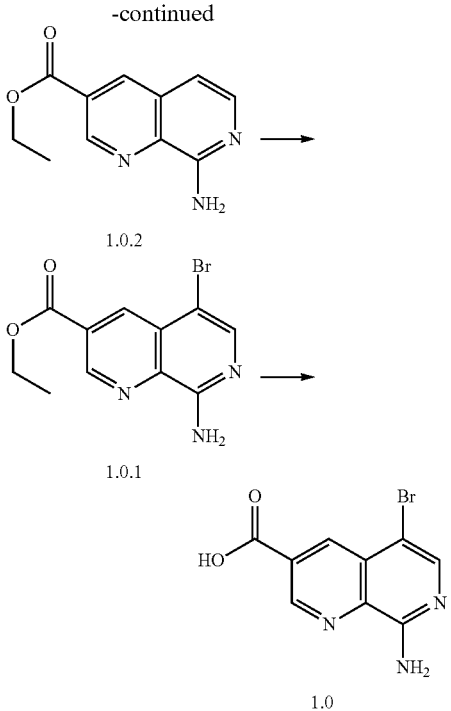

Step 1.

A solution of 3-amino-2-chloropyridine (5.00 g, 39 mmol) in 50 ml of THF was added dropwise to 43 ml of a 2M solution of NaHMDS (86 mmol) in THF at −10° C. under nitrogen stream. The reaction mixture was incubated at 0° C. for 10 minutes, then a solution of di-tert-butyl dicarbonate (8.91 g, 41 mmol) in 20 ml of THF was added dropwise at such a rate that the temperature did not exceed 8° C. After 30 minutes, 150 ml of 1M aqueous HCl solution and 50 ml of ethyl acetate were added. The organic layer was washed with water and concentrated in vacuo. Product 1.0.6 was isolated as light yellow powder by column chromatography on silica gel using hexane-dichloromethane-ethylacetate (8:2:0.5) as eluent. Yield: 8.10 r (91%).

Step 2.

4.33 ml of TMEDA (29 mmol) was added under a stream of nitrogen to solution 1.0.6 (3.00 g, 13 mmol) in 50 ml of THF, 11.5 ml of 2.5 M butyl lithium solution (29 mmol) in hexane was cooled to −78° C. and added dropwise. At the end of the addition, the reaction mixture was kept at −70° C. for 40 min and 20 min at −20° C. After cooling again to −78° C., DMF (2.03 ml, 26 mmol) was added dropwise. After keeping the reaction mixture at −70° C. for 1 h, it was heated to −20° C. and 50 ml of a saturated $NH_4Cl$ aqueous solution of was added. 20 mL of water and 50 ml of ethyl acetate were added to the resulting mixture. The organic layer was separated, washed with water and concentrated in vacuo. Product 1.0.5 was isolated as yellow oil by column chromatography on silica gel using hexane-ethyl acetate (8:2) as eluent. Yield: 2.86 r (85%).

Step 3.

Ethyl 3,3-diethoxypropionate (1.14 ml, 5.79 mol) and trifluoroacetic acid (3.54 ml, 46 mmol) were added to a solution of compound 1.0.5 (1.00 g, 3.86 mol) in 10 ml of chloroform, the solution was then boiled for 30 minutes. After cooling the reaction mixture to room temperature, solvents were distilled off under reduced pressure. The mixture was then boiled in 5 ml of thionyl chloride for 1 h. A saturated solution of $NaHCO_3$ was added to the reaction mixture to pH 9, extraction was performed by ethyl acetate. The organic extracts were combined, solvent was evaporated under reduced pressure. Product 1.0.4 was isolated as light-yellow powder by column chromatography on silica gel using hexane-ethyl acetate (8:2) as eluent. Yield: 502 mg (55%).

Step 4.

$Cs_2CO_3$ (5.97 g, 18.1 mol), BINAP (570 mg, 0.10 eq.), Palladium (II) acetate (103 mg, 0.05 eq.), 1.2 ml of 1M tert-butyl carbamate solution (13.6 mol, 1.50 eq.) were added to a solution of compound 1.0.4 (2.16 g, 9.06 mol) in 30 ml of 1,4-dioxane, the solution was then heated to 100° C. for 1.5 h. The reaction mixture was cooled to room temperature and filtered through Celite. Solvents were distilled off in vacuo, residue was dissolved in dichloromethane, washed with water and concentrated in vacuo. Product 1.0.3 was isolated by column chromatography on silica gel using dichloromethane-ethylacetate (96:4) as eluent. Yield: 2.73 r (95%).

Step 5:

Compound 1.0.3 (2.80 g, 7.50 mol) was dissolved in dichloromethane and 18 ml of HCl solution in 1,4-dioxane was added. After 2 hours, solvents were distilled off under reduced pressure, a saturated $NaHCO_3$ solution was added to the residue. The precipitate was filtered and washed with a mixture of hexane-ethylacetate (1:1), product was 1.0.2 obtained as white powder. Yield: 1.60 r (98%).

Step 6.

N-bromosuccinimide (1.38 g, 7.73 mol) was added to a suspension of compound 1.0.2 (1.60 g, 7.37 mol) in 15 ml of DMF, the solution was then stirred at room temperature for 1 h. 100 ml of water and 5 ml of a saturated $NaHCO_3$ solution were added to the resulting solution. The precipitate of product 1.0.1 was filtered off Yield: 1.95 r (89%).

Step 7.

A solution of $LiOH \times H_2O$ (156 mg, 3.68 mmol, 1.1 eq.) in 7 ml of water was added to a solution of compound 1.0.1 (1.00 g, 3.34 mmol, 1.00 eq.) in 7 ml of THF. After one hour of stirring at room temperature, THF was distilled off under reduced pressure, pH of the solution was adjusted to 4 with 1M HCl solution, the brown precipitate of product 1.0 was filtered off, washed with water and dried under heating and reduced pressure. Yield: 870 mg (97%).

Example 2. Method of Preparation of Compounds 1.1, 1.2, 1.3, 1.4, 1.5

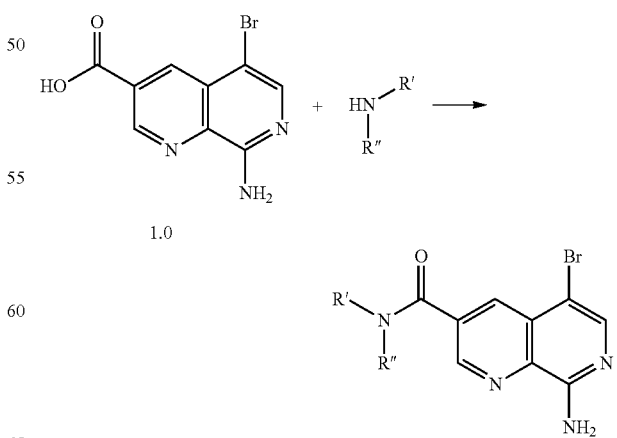

-continued

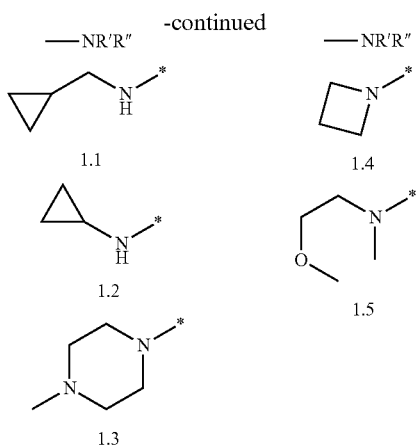

EDC×HCl (212 mg, 1.11 mmol) was added portionwise under cooling in an ice bath to a suspension of compound 1.0 (200 mg, 0.739 mmol), cyclopropanemethylamine (128 µl, 1.48 mmol), HOBt (170 mg, 1.11 mmol) and triethylamine (206 µl, 1.48 mmol) in 3 ml of DMF. After 15 h, solvent was distilled off under reduced pressure. Product 1.1 was isolated by column chromatography on silica gel using hexane-dichloromethane-methanol (5:4:1) as eluent. Yield: 178 mg (75%).

Compounds 1.2, 1.3, 1.4 and 1.5 were prepared similarly from the corresponding initial compounds.

Example 3. Method of Preparation of Compound 2.0

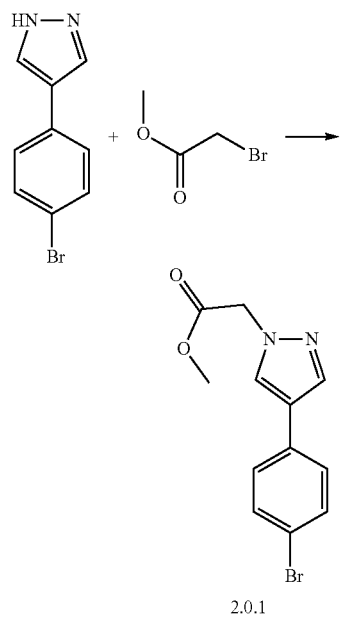

Step 1.

4-(4-bromophenyl)pyrazole (500 mg, 2.23 mmol) and methyl 2-bromoacetate (340 mg, 2.23 mmol) were mixed in dry acetone and degassed. Then, crushed anhydrous $K_2CO_3$ was added to the reaction mixture, the mixture was boiled under stirring for 8 hours. The reaction mass was filtered off, passed through silica gel, concentrated in vacuo and recrystallized from the mixture of hexane-dichloromethane (1:1). Product 2.0.1 as a yellow powder was obtained. Yield: 480 mg (73%).

Step 2.

Ether 2.0.1 (1.07 g, 3.63 mmol) and LiOH H$_2$O (225 mg, 5.37 mmol) in a mixture of THF-water were stirred at room temperature for 1 h. The reaction mixture was then treated with methyl tert-butyl ether, the aqueous layer was acidified to pH=1.5, white precipitate of product 2.0 was filtered off and dried in air. Yield: 720 mg (80%).

Example 4. Method of Preparation of Compounds 2.1 and 2.2

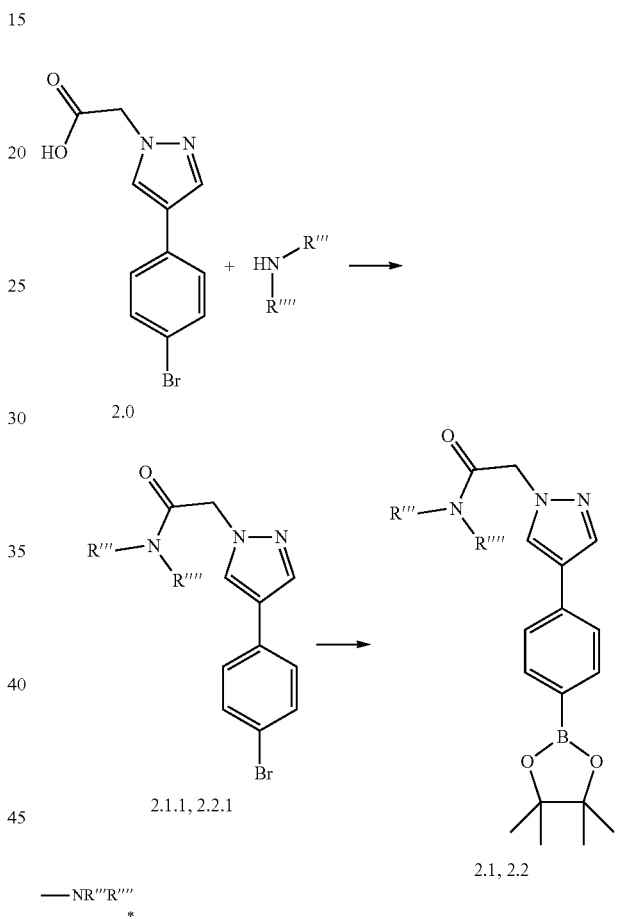

Step 1.

A mixture of acid 2.0 (720 mg, 2.56 mmol), dimethylamine hydrochloride (250 mg, 3.07 mmol), EDC×HCl (589 mg, 3.07 mmol), DMAP (78 mg, 0.64 mmol) and triethylamine (357 µl, 2.56 mmol) in dichloromethane in a nitrogen atmosphere was stirred for 2 h. The reaction mixture was then concentrated under reduced pressure, and product 2.1.1 as white powder was isolated by column chromatography using the mixture of dichloromethane-methanol (9:1) as eluent. Yield: 420 mg (53%).

Compound 2.2.1 was prepared similarly from the corresponding initial compounds.

Step 2.

A mixture of compound 2.1.1 (680 mg, 2.19 mmol), bis-pinacoldiborane (690 mg, 2.64 mmol) and anhydrous potassium acetate (650 mg, 6.59 mmol) in 10 ml of 1,4-dioxane was degassed with nitrogen for 15 minutes. PddppfCl$_2$×DCM (90 mg, 0.01 mmol) was then added to the mixture, the mixture was boiled under stirring under nitrogen atmosphere for 12 h. The reaction mixture was then filtered through Celite and concentrated in vacuo. The mixture was washed with water, extraction was performed with methylene chloride. Product 2.1 was isolated by column chromatography using a mixture of ethyl acetate-methanol (9:1). Yield: 350 mg (45%).

Compound 2.2 was prepared similarly from the corresponding initial compounds.

Example 5. Method of Preparation of Compound 2.3

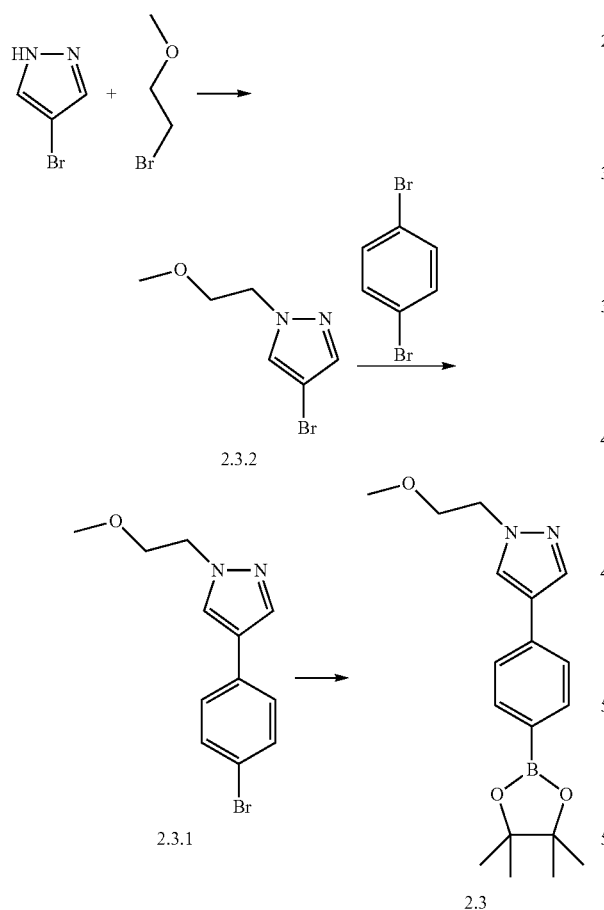

Step 1.

3-Bromo-1H-pyrazole (5.00 g, 33.7 mmol) was dissolved in 25 ml of ethanol, 1-bromo-2-methoxyethane (4.71 ml, 50.5 mmol) and KOH (2.86 g 50.5 mmol) were added. The reaction mixture was boiled under stirring for 6 h. The reaction mixture was then concentrated in vacuo, treated with water, and product 2.3.2 as a yellow oil was isolated by extraction. Yield was 6.23 g (90%).

Step 2.

Nitrogen was passed for 15 minutes through a mixture of bromopyrazole 2.3.2 (6.19 g, 29.9 mmol), bis-pinacoldiborane (9.11 g, 35.8 mmol) and anhydrous potassium acetate (8.80 g, 89.7 mmole) in 50 ml of 1,4-dioxane. PddppfCl$_2$×DCM (1.26 mg, 1.49 mmol) was then added to the mixture, the mixture was boiled under stirring under nitrogen atmosphere for 5 h. Then, 1,4-dibromobenzene (14.1 g, 59.8 mmol), a solution of Cs$_2$CO$_3$ (19.5 g, 59.8 mmol) in 50 ml of water was added, and the reaction mixture was degassed with nitrogen for 15 minutes. Pd(PPh$_3$)$_4$ (1.73 g, 15.9 mmol) was added to the reaction mass, the mass was boiled under stirring under nitrogen atmosphere for 4 h. The reaction mixture was then filtered through Celite, concentrated under reduced pressure, treated with water, extracted by ethyl acetate, and bromophenylpyrazole 2.3.1 was isolated by column chromatography using hexane-ethyl acetate (1:1) as eluent. Yield: 3.11 r (38%).

Step 3.

Compound 2.3 was prepared in a similar fashion to compound 2.1 (example 4, step 2).

Example 5. Method of Preparation of Compounds 3.43, 3.44, 3.45, 3.46, 3.47, 3.48, 3.49, 3.50, 3.51, 3.52, 3.53, 3.54, 3.55, 3.56, 3.57

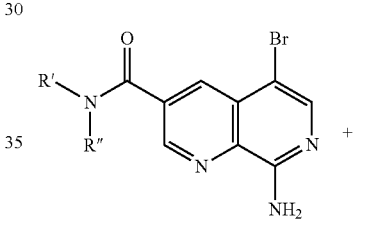

37
-continued

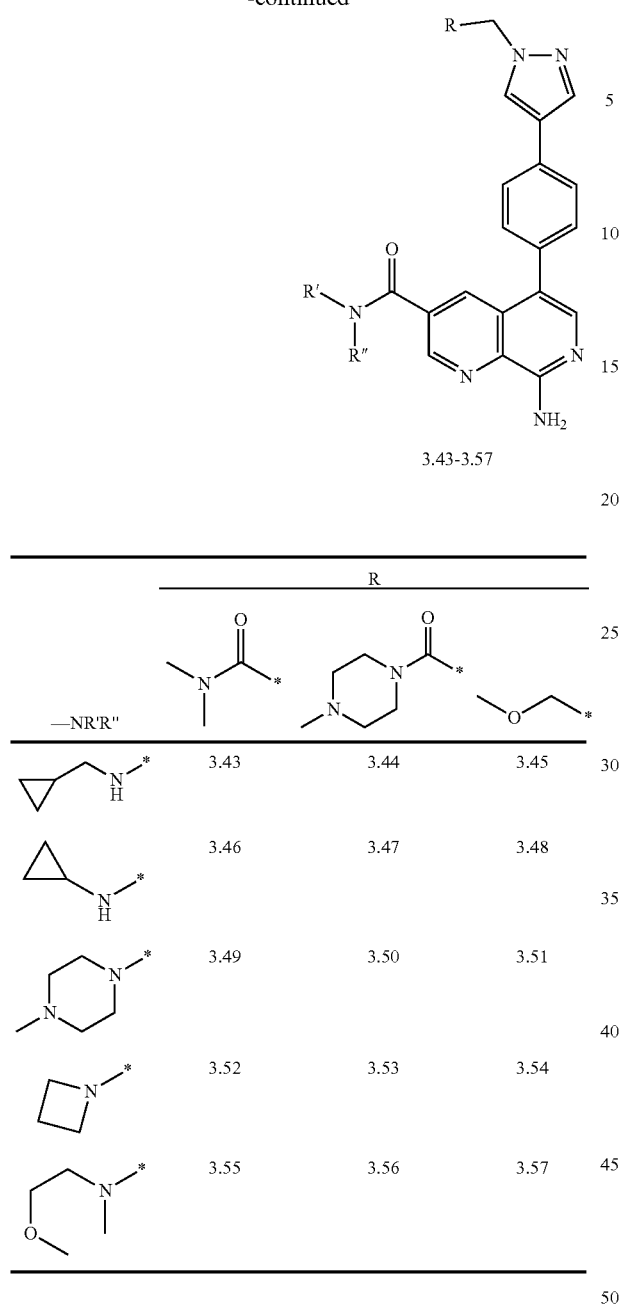

3.43-3.57

| —NR'R" | R | | |
|---|---|---|---|
| | ![Me-N(Me)-C(O)-] | ![MeN-piperazine-C(O)-] | ![MeO-CH2-] |
| cyclopropyl-CH2-NH-* | 3.43 | 3.44 | 3.45 |
| cyclopropyl-NH-* | 3.46 | 3.47 | 3.48 |
| 4-methylpiperazin-1-yl-* | 3.49 | 3.50 | 3.51 |
| azetidin-1-yl-* | 3.52 | 3.53 | 3.54 |
| MeO-CH2CH2-N(Me)-* | 3.55 | 3.56 | 3.57 |

A solution of compound 1.1 (200 mg, 0.623 mmol), compound 2.1 (355 mg, 0.747 mmol) and NaHCO$_3$ (157 mg, 1.87 mmol) in a mixture of 10 ml of 1,4-dioxane and 5 ml of water was degassed with a nitrogen stream, Pd(PPh$_3$)$_4$ (72 mg, 0.1 eq.) was then added. The reaction mass was heated at 90° C. for 5 hours, after which volatile compounds were evaporated under reduced pressure. The residue was dissolved in ethyl acetate, washed with water and concentrated in vacuo. The product was isolated by column chromatography on silica gel using dichloromethane-ethylacetate-methanol (4:6:1) as eluent. Compound 3.43 was further purified by preparative chromatography. Yield: 150 mg (51%).

Compounds 3.44, 3.45, 3.46, 3.47, 3.48, 3.49, 3.50, 3.51, 3.52, 3.53, 3.54, 3.55, 3.56 and 3.57 were prepared in a similar way.

38

Example 6. Method of Preparation of Compound 3.49×2HCl

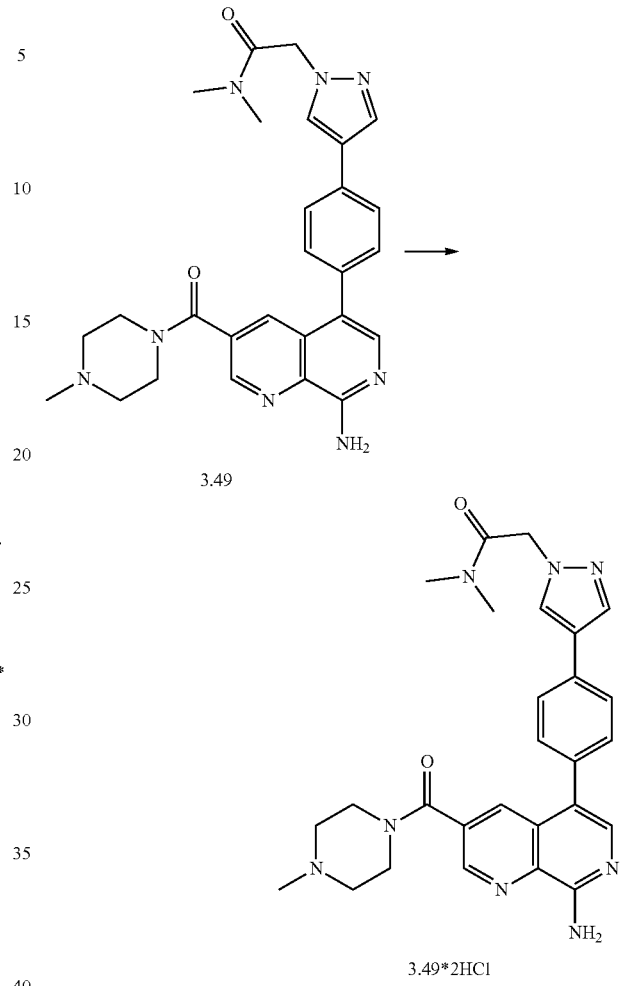

A 0.4 M HCl solution in diethyl ether (188 µl, 0.075 mmol, 2.5 eq.) was added dropwise under a nitrogen stream to a solution of compound 3.49 (15 mg, 0.030 mmol) in the mixture of dichloromethane-methanol (10:1). Volatile components were distilled off under reduced pressure, the resulting solid residue was triturated with diethyl ether. Yellow precipitate was filtered off, washed twice with ether, dried in vacuo. Yield: 16 mg (100%).

Example 7. Analysis of Prepared Compounds

Purity and structure of the prepared compounds were confirmed by liquid chromatography-mass spectrometry (LC-MS) and $^1$H NMR spectroscopy (Table 1).

TABLE 1

Physicochemical properties of candidates

| Compound No. | ESI-MS. [M + H]$^+$ | $^1$H NMR (400 MHZ, DMSO-d6), δ, MD |
|---|---|---|
| 3.43 | 470.2 | 9.19 (d, J = 2.0 Hz, 1H), 8.99 (t, J = 5.5 Hz, 1H), 8.55 (d, J = 2.0 Hz, 1H), 8.16 (s, 1H), 7.96 (s, 1H), 7.95 (s, 1H), 7.73 (d, J = 8.2 Hz, 2H), 7.49 (d, J = 8.2 Hz, 2H), 7.16 (s, 2H), 5.16 (s, 2H), 3.18 (t, J = |

TABLE 1-continued

Physicochemical properties of candidates

| Compound No. | ESI-MS. [M + H]+ | 1H NMR (400 MHZ, DMSO-d6), δ, MD |
|---|---|---|
| 3.44 | 263.2 [M + 2H]2+/2, 525.3 | 6.2 Hz, 2H), 3.07 (s, 3H), 2.89 (s, 3H), 1.12-0.96 (m, 1H), 0.49-0.38 (m, 2H), 0.31-0.14 (m, 2H). 9.19 (d, J = 1.9 Hz, 1H), 9.08-8.94 (m, 1H), 8.55 (d, J = 1.9 Hz, 1H), 8.17 (s, 1H), 7.96 (d, J = 7.5 Hz, 2H), 7.73 (d, J = 8.1 Hz, 2H), 7.49 (d, J = 8.1 Hz, 2H), 7.16 (s, 2H), 5.18 (s, 2H), 3.56-3.42 (m, 4H), 3.18 (t, J = 6.1 Hz, 2H), 2.43-2.26 (m, 4H), 2.22 (s, 3H), 1.11-1.00 (m, 1H), 0.50-0.38 (m, 2H), 0.29-0.17 (m, 2H). |
| 3.45 | 443.2 | 9.19 (d, J = 2.0 Hz, 1H), 8.99 (t, J = 5.6 Hz, 1H), 8.54 (d, J = 2.0 Hz, 1H), 8.23 (s, 1H), 7.97 (s, 1H), 7.95 (s, 1H), 7.73 (d, J = 8.2 Hz, 2H), 7.48 (d, J = 8.2 Hz, 2H), 7.15 (s, 2H), 4.31 (t, J = 5.3 Hz, 2H), 3.75 (t, J = 5.3 Hz, 2H), 3.27 (s, 3H), 3.18 (t, J = 6.2 Hz, 2H), 1.12-0.97 (m, 1H), 0.48-0.40 (m, 2H), 0.29-0.17 (m, 2H). |
| 3.46 | 456.2 | 9.14 (d, J = 1.8 Hz, 1H), 8.87 (d, J = 3.9 Hz, 1H), 8.52 (d, J = 1.9 Hz, 1H), 8.21-8.07 (m, 1H), 7.96 (d, J = 7.3 Hz, 2H), 7.73 (d, J = 8.1 Hz, 2H), 7.48 (d, J = 8.1 Hz, 2H), 7.16 (s, 2H), 5.16 (s, 2H), 3.07 (s, 3H), 2.94-2.83 (m, 4H), 0.77-0.68 (m, 2H), 0.63-0.54 (m, 2H). |
| 3.47 | 256.2 [M + 2H]2+/2, 511.2 | 9.14 (d, J = 2.0 Hz, 1H), 8.88 (d, J = 4.0 Hz, 1H), 8.52 (d, J = 2.0 Hz, 1H), 8.18 (s, 1H), 7.97 (s, 1H), 7.95 (s, 1H), 7.73 (d, J = 8.2 Hz, 2H), 7.48 (d, J = 8.2 Hz, 2H), 7.15 (s, 2H), 5.18 (s, 2H), 3.55-3.47 (m, 4H), 2.90-2.84 (m, 1H), 2.39-2.27 (m, 4H), 2.21 (s, 3H), 0.75-0.69 (m, 2H), 0.62-0.56 (m, 2H). |
| 3.48 | 429.2 | 9.14 (d, J = 2.0 Hz, 1H), 8.87 (d, J = 3.9 Hz, 1H), 8.51 (d, J = 2.0 Hz, 1H), 8.24 (s, 1H), 7.97 (s, 1H), 7.94 (s, 1H), 7.72 (d, J = 8.2 Hz, 2H), 7.47 (d, J = 8.2 Hz, 2H), 7.15 (s, 2H), 4.31 (t, J = 5.3 Hz, 2H), 3.75 (t, J = 5.3 Hz, 2H), 3.27 (s, 3H), 2.88-2.85 (m, 1H), 0.76-0.68 (m, 2H), 0.65-0.56 (m, 2H). |
| 3.49 | 250.2 [M + 2H]2+/2, 499.3 | 8.83 (d, J = 1.9 Hz, 1H), 8.14 (s, 1H), 8.09 (d, J = 1.9 Hz, 1H), 7.95 (d, J = 3.2 Hz, 2H), 7.72 (d, J = 8.2 Hz, 2H), 7.46 (d, J = 8.2 Hz, 2H), 7.15 (s, 2H), 5.15 (s, 2H), 3.74-3.51 (m, 2H), 3.51-3.30 (m, 2H), 3.07 (s, 3H), 2.88 (s, 3H), 2.41-2.20 (m, 4H), 2.19 (s, 3H). |
| 3.49 × 2HCl | 250.2 [M + 2H]2+/2, 499.3 | 11.42 (br s, 1H), 9.10 (d, J = 1.8 Hz, 1H), 8.27 (d, J = 1.8 Hz, 1H), 8.19 (s, 1H), 7.99 (s, 1H), 7.87 (s, 1H), 7.79 (d, J = 8.3 Hz, 2H), 7.51 (d, J = 8.3 Hz, 2H), 5.17 (s, 2H), 4.61-4.45 (m, 1H), 3.82-3.22 (m, 8H), 3.20-2.99 (m, 2H), 3.07 (s, 3H), 2.88 (s, 3H), 2.74 (s, 3H). |
| 3.50 | 185.5 [M + 3H]3+/3, 277.8 [M + 2H]2+/2, 554.3 | 8.83 (d, J = 1.9 Hz, 1H), 8.16 (s, 1H), 8.08 (d, J = 1.9 Hz, 1H), 7.96 (s, 2H), 7.72 (d, J = 8.2 Hz, 2H), 7.46 (d, J = 8.2 Hz, 2H), 7.14 (s, 2H), 5.18 (s, 2H), 3.70-3.35 (m, 8H), 2.41-2.24 (m, 8H), 2.21 (s, 3H), 2.19 (s, 3H). |
| 3.51 | 236.6 [M + 2H]2+/2, 472.1 | 8.83 (d, J = 1.9 Hz, 1H), 8.22 (s, 1H), 8.08 (d, J = 1.9 Hz, 1H), 7.95 (s, 2H), 7.72 (d, J = 8.2 Hz, 2H), 7.46 (d, J = 8.2 Hz, 2H), 7.15 (s, 2H), 4.30 (t, J = 5.3 Hz, 2H), 3.74 (t, J = 5.3 Hz, 2H), 3.71-3.58 (m, 2H), 3.46-3.30 (m, 2H), 3.26 (s, 3H), 2.42-2.30 (m, 2H), 2.30-2.18 (m, 2H), 2.19 (s, 3H). |
| 3.52 | 456.2 | 9.00 (d, J = 2.0 Hz, 1H), 8.28 (d, J =2.0 Hz, 1H), 8.16 (s, 1H), 7.96 (s, 2H), 7.74 (d, J = 8.2 Hz, 2H), 7.47 (d, J = 8.2 Hz, 2H), 7.23 (s, 2H), 5.16 (s, 2H), 4.32 (t, J = 7.6 Hz, 2H), 4.08 (t, J = 7.7 Hz, 2H), 3.07 (s, 3H), 2.89 (s, 3H), 2.35-2.25 (m, 2H). |
| 3.53 | 256.2 [M + 2H]2+/2, 511.2 | 8.99 (d, J = 1.8 Hz, 1H), 8.28 (d, J = 1.9 Hz, 1H), 8.17 (s, 1H), 7.97 (s, 2H), 7.74 (d, J = 8.1 Hz, 2H), 7.47 (d, J = 8.1 Hz, 2H), 7.16 (s, 2H), 5.18 (s, 2H), 4.33 (t, J = 7.5 Hz, 2H), 4.08 (t, J = 7.6 Hz, 2H), 3.59-3.42 (m, 4H), 2.41-2.25 (m, 6H), 2.22 (s, 3H). |
| 3.54 | 429.1 | 8.99 (d, J = 1.9 Hz, 1H), 8.28 (d, J = 1.9 Hz, 1H), 8.24 (s, 1H), 7.97 (s, 1H), 7.96 (s, 1H), 7.73 (d, J = 8.2 Hz, 2H), 7.46 (d, J = 8.2 Hz, 2H), 7.23 (s, 1H), 4.37-4.27 (m, 4H), 4.08 (t, J = 7.7 Hz, 2H), 3.75 (t, J = 5.3 Hz, 2H), 3.27 (s, 3H), 2.33-2.25 (m, 2H). |
| 3.55 | 488.3 | 8.87-8.77 (m, 1H), 8.17-8.06 (m, 2H), 7.97-7.91 (m, 2H), 7.72 (d, J = 8.2 Hz, 2H), 7.49-7.42 (m, 2H), 7.13 (br s, 2H), 5.15 (s, 2H), 3.68-3.54 (m, 1H), 3.38 (s, 3H), 3.29-3.26 (s, 3H), 3.07 (s, 3H), 3.07-3.03 (m, 2H), 2.99 (s, 3H), 2.88 (s, 3H). |
| 3.56 | 272.3 [M + 2H]2+/2, 543.3 | 8.85-8.76 (m, 1H), 8.20-8.08 (m, 2H), 7.95 (s, 1H), 7.92 (s, 1H), 7.72 (d, J = 8.2 Hz, 2H), 7.48-7.41 (m, 2H), 7.14 (br s, 2H), 5.17 (s, 2H), 3.67-3.56 (m, 1H), 3.56-3.45 (m, 4H), 3.38 (s, 3H), 3.30-3.24 (m, 1H), 3.10-3.02 (m, 2H), 2.99 (s, 3H), 2.40-2.26 (m, 4H), 2.21 (s, 3H). |
| 3.57 | 461.3 | 8.85-8.76 (m, 1H), 8.22 (s, 1H) 8.15-8.06 (m, 1H), 7.95 (s, 1H), 7.94 (s, 1H), 7.71 (d, J = 5.3 Hz, 2H), 7.49-7.40 (m, 2H), 7.13 (br s, 2H), 4.30 (t, J = 5.3 Hz, 2H), 3.74 (t, J = 5.3 Hz, 2H), 3.67-3.53 (m, 1H), 3.38 (s, 3H), 3.29-3.26 (m, 1H), 3.26 (s, 3H), 3.09-3.03 (m, 2H), 2.99 (s, 3H). |

Example 8. Determination of Stability of the Compounds in Human Blood Plasma

To assess the blood plasma stability of the compounds, we used pooled human blood plasma taken from ten healthy donors. The initial candidate solution (10 mM in DMSO) was diluted with pooled blood plasma to a concentration of 10 μm (test solution). The test solution was incubated in a dry block thermostat for 4 hours at 37° C. HPLC with Agilent 1200 liquid chromatography system (Agilent, USA) was employed to determine peak areas of the compounds in test samples, said peak areas corresponding to the initial test time (prior to incubation) and the final test time (after incubation in a dry block thermostat for 4 hours at 37° C.), proteins were preliminarily precipitated with acetonitrile. Chromatographic analysis was performed in a gradient elution regime with a flow rate of 1 mL/min Substance amount in % in a sample after thermostatting was determined.

The stability of the compounds was estimated. The compounds described herein show at least 90% chemical stability, i.e. they are chemically stable in human blood plasma (Table 2).

TABLE 2

Results of determination of stability of compounds in human blood plasma. The results are presented as average values of stability of compounds (%) obtained in several tests.

| Compound No. | Chemical stability in human blood plasma 4 h, % |
|---|---|
| 3.43 | 100.0 |
| 3.44 | 100.0 |
| 3.45 | 91.2 |
| 3.46 | 96.5 |
| 3.47 | 96.5 |
| 3.48 | 98.4 |
| 3.49 | 100.0 |
| 3.51 | 100.0 |
| 3.52 | 100.0 |
| 3.53 | 100.0 |
| 3.54 | 94.6 |

Example 9. Determination of Enzyme Stability

Measuring of enzyme stability of the present compounds enabled estimation of their stability towards the action of Phase I biotransformation enzymes.

The rate of enzymatic decomposition of a compound was detected by incubating the reaction mixture in a dry block heater at 37° C.; the reaction mixture contained 0.5 mg/mL of pooled human liver microsomes (XenoTech, USA, cat #H6010), 10 µM of a compound, 2 mM β-nicotinamide adenine dinucleotide (Carbosynth, UK, cat #NN10871) and 4 mM of magnesium chloride in 0.1M sodium phosphate buffer (pH=7.4). The reaction was quenched with acetonitrile (100 µL of acetonitrile/100 µL of the reaction mixture). After quenching, the samples were centrifuged at 10000 rpm for 10 minutes. Supernatant fluid was tested by chromatographic technique using Agilent1200 (Agilent, USA). Chromatographic analysis was performed in a gradient elution regime with a flow rate of 1 mL/min. A graph of the logarithm of substance's peak area as a function of time was made. The dependent factor of the line corresponded to the elimination rate constant K based on which the drug's half-lif½e T and degradation rate $CL_{int}$ were calculated:

$$\text{Elimination rate constant } (k) = (-\text{gradient})$$

$$\text{Half life } (t_{1/2})(\text{min}) = \frac{0.693}{k}$$

$$V(\mu L/mg) = \frac{\text{volume of incubation } (\mu L)}{\text{protein in the incubation (mg)}}$$

$$\text{Intrinsic Clearance } (CL_{ml})(\mu L/\text{min mg protein}) = \frac{V \times 0.693}{t_{1/2}}$$

Based on the data obtained, candidates' enzyme stability in human liver microsomes was determined. The compounds according to the present invention showed sufficient stability towards the action of Phase I biotransformation enzymes and enzyme degradation rate $CL_{int}$ of less than 47 µL/min/mg. The results are shown in Table 3.

Measuring of enzyme stability of the present compounds enabled estimation of their stability towards the action of Phase II biotransformation enzymes.

Enzyme degradation rate was measured by incubating the reaction mixture in a dry block thermostat at 37° C., said reaction mixture comprising 0.5 mg/mL of pooled human liver S9 fractions (XenoTech, USA, cat #H0610), 10 µM compound, 2 mM β-nicotinamide adenine dinucleotide (Carbosynth, UK, cat #NN10871) and 4 mM magnesium chloride in 0, 1 M sodium-phosphate buffer, pH=7, 4. The reaction was quenched with acetonitrile (100 µL of acetonitrile/100 µL of the reaction mixture). After quenching, the samples were centrifuged at 10000 rpm for 10 minutes. Supernatant fluid was tested by chromatographic technique using Agilent1200 (Agilent, USA). Chromatographic analysis was performed in a gradient elution regime with a flow rate of 1 mL/min A graph of the logarithm of substance's peak area as a function of time was made. The dependent factor of the line corresponded to the elimination rate constant K based on which the drug's half-life T½ and degradation rate CLint were calculated:

$$\text{Elimination rate constant } (k) = (-\text{gradient})$$

$$\text{Half life } (t_{1/2})(\text{min}) = \frac{0.693}{k}$$

$$V(\mu L/mg) = \frac{\text{volume of incubation } (\mu L)}{\text{protein in the incubation (mg)}}$$

$$\text{Intrinsic Clearance } (CL_{ml})(\mu L/\text{min mg protein}) = \frac{V \times 0.693}{t_{1/2}}$$

Based on the data obtained, candidates' enzyme stability in human liver S9 fractions was determined. The compounds demonstrate sufficient microsomal stability and their rate of enzymatic decomposition Clint is less than 24 µL/min/mg. The results are shown in Table 3.

TABLE 3

Results of measurement of enzyme stability of compounds. The results are presented as average values of stability of compounds ($CL_{int}$, µL/min/mg) obtained in several tests.

| Compound No. | Enzyme stability $CL_{int}$, µL/min/mg | |
|---|---|---|
| | Liver S9 fraction | Human liver microsomes |
| 3.45 | 1.1 | 39.6 |
| 3.46 | 0.5 | 2.6 |
| 3.47 | 1.5 | 5.6 |
| 3.48 | 2.5 | 18.0 |
| 3.49 | 1.4 | 7.0 |
| 3.52 | 2.4 | 7.0 |
| 3.53 | 7.1 | 7.8 |

Example 10. Estimation of Permeability of Compounds Through Caco-2 Cell Monolayer Estimation of permeability through Caco-2 cell monolayer enables assessment of the ability of the substances to penetrate through biological membranes by means of both active and passive transport.

Intestinal epithelial cells Caco-2 were grown on filter inserts (pore size 0.4 jam, BD Falcon with High Density) for 21 days; monolayer integrity was then checked using Lucifer Yellow (Sigma-Aldrich, USA) according to the standard protocol. In A→B transfer ("intestinal lumen"-"blood stream" transfer), solutions of the test substances in buffer, pH 6.5 (HBSS, 10 mM HEPES, 15 mM glucose) at a concentration of 10 µM were added to the upper chamber; whereas the lower chamber was filled with buffer, pH 7.4 (HBSS, 10 mM HEPES, 15 mM Glucose, 1% BSA). In B→A transfer ("blood stream"-"intestinal lumen" transfer), the upper chamber was filled with buffer, pH 6.5, whereas the solutions of the test substances in buffer, pH 7.4, at a concentration of 10 µM were added to the lower chamber. A highly permeable substance propranolol was used as a control.

After 2 hour incubation at 37° C. under an atmosphere containing 5% $CO_2$, the amounts of the test substances in the upper and lower chambers were measured by HPLC using an Agilent1200 HPLC system (Agilent, USA), proteins were preliminarily precipitated with acetonitrile. Chromatographic analysis was performed in a gradient elution regime with a flow rate of 1 mL/min. The peak areas corresponding to the compounds were detected on chromatograms. Based on the peak areas of a compound in the calibration standards, concentration of the compound in the initial solution and in the samples from upper chamber wells and lower chamber wells was measured.

Cellular permeability coefficient Papp was calculated by the formula:

$$P_{app}=(C_{a(t)}*Va)/(C_{d(0)}*t*\text{Area}), \text{ where}$$

$P_{app}$ is the effective permeability constant, m/s
V is the volume of solution (0.8 ml in A→B test, 0.2 ml in B→A test), ml
Area is the membrane surface area (0.33 cm$^2$), cm$^2$
t is the time of incubation (7200 sec), sec
$C_{d(0)}$ is the initial solution concentration, μM
$C_{a(t)}$ is the concentration of the solution after 2 hours (the concentration in the sample from the well of the lower chamber in A→B test; the concentration in the sample from the well of the top chamber in in B→A test), μM The efflux coefficient showed that cells were capable of eliminating a substance from blood stream. The value was calculated by the following formula:

$$\text{efflux}=P_{app\ B-A}/P_{app\ A-B}, \text{ where}$$

$P_{ape\ A-B}$-direct A→B test permeability value
$P_{app\ B-A}$-reverse B→A test permeability value The compounds of the present invention showed high rate of direct transport, efflux coefficient being not more than 2. Based on the result, we can assume that Pgp transporter does not impose restrictions on substance bioavailability. The results are shown in Table 4.

TABLE 4

The Results of measurement of permeability through Caco-2 cell monolayer. Results are presented as average values of direct transport (A→B, Paap 10$^{-6}$ cm/s) and Efflux of compounds obtained in several tests.

| Compound No. | A→B Papp 10$^{-6}$ cm/s | Efflux |
|---|---|---|
| 3.43 | 15.68 | 1.89 |
| 3.45 | 34.48 | 0.37 |
| 3.48 | 36.19 | 0.64 |
| 3.51 | 26.23 | 1.88 |
| 3.52 | 18.74 | 1.66 |
| 3.54 | 42.78 | 0.55 |

Example 11. Affinity of Compounds to Recombinant CDK8 Protein-Cyclin C Complex In Vitro Capability of compounds of the present invention to bind to CDK8 protein was detected using LanthaScreen (ThermoFisher) assay. We detected FRET signal proportional to the amount of CDK8-bound fluorescently-labeled ligand (Tracer 236) that competes with inhibitor for ATP binding site. We carried out the measurements in a 15 μl reaction volume using a 384-well plate (Corning, #CLS4513). Enzyme CDK8/Cyclin C (ThermoFisher, #PR7261B) was mixed with antibodies Anti-His-tag-Biotin (ThermoFisher, #PV6090), Streptavidin-Eu (ThermoFisher, #PV6025), the resulting mixture was added to plate wells (5 мкπ/well). Final concentrations of substances were as follows: CDK8/Cyclin C—5 nM, Streptavidin-Eu—3 nM, Anti-His-tag-Biotin—3 nM. Staurosporine (S4400, Sigma) was used as a reference inhibitor, and 0.1% solution of dimethyl sulphoxide (DMSO) in reaction buffer was used as a blank, the reaction buffer comprised 250 mM HEPES (pH 7.5), 50 mM MgCl2, 5 mM EGTA, and 0.05% Brij-35. The inhibitors and controls in question were added to corresponding wells (5 μl/well). The plate was incubated at room temperature for 20 minutes. After incubating, 5 μl/well of tracer solution Alexa Fluor-647 (Kinase Tracer 236, ThermoFisher, #PV5592)) was added to the wells. Final concentration of tracer was 10 nM. Reaction buffer, instead of tracer solution, was used as a negative control. The plate was incubated for 40 minutes at 25° C., TR-FRET signal was then measured according to the manufacturer's guidelines on SPARK20 plate reader (Tecan, Switzerland), and the value was converted to the amount of kinase-bound tracer. IC$_{50}$ values were calculated using SparkControl Magellan 1.2 software (Tecan, Switzerland) approximating experimental points by four-parameter logistic model with the optimization by Levenberg-Marquardt (Table 5).

TABLE 5

The Results of biochemical assay of binding of compounds to CDK8/Cyclin C protein. Data is presented as average values of IC$_{50}$ obtained in several tests.

| Compound no. | CDK8/Cyclin C IC$_{50}$, nM |
|---|---|
| 3.43 | 0.88 |
| 3.44 | 1.40 |
| 3.45 | 1.63 |
| 3.46 | 1.11 |
| 3.47 | 1.10 |
| 3.48 | 1.10 |
| 3.49 | 1.85 |
| 3.49 × 2HCl | 1.64 |
| 3.50 | 2.03 |
| 3.51 | 1.44 |
| 3.52 | 0.96 |
| 3.53 | 1.01 |
| 3.54 | 1.27 |
| 3.55 | 1.24 |
| 3.56 | 1.07 |
| 3.57 | 2.27 |

Example 12. Antiproliferative Activity Towards CDK8-Sensitive Cell Lines In Vitro Antiproliferative activity of CDK8 inhibitors according to the present invention was measured in a cell-based test on continuous cell cultures MV4-11 (biphenotypic myelomonocytic leukemia, ATCC® CRL-9591™), KG-1 (acute myeloid leukemia, ATCC® CCL-246™) using a vital stain AlamarBlue (ThermoFisher, #DAL1100). The cells were grown in RPMI-1640 (PanEco, #C$_{330}$p) medium with addition of 10% FBS (Gibco, #16140-071); washed and resuspended in culture medium with 10% FBS (Gibco, #16140-071) in 96-well culture plates (Corning, #3599) with ≈10× 10$^3$ cells in 100 μm of medium per well. The compounds in question were dissolved in DMSO and diluted with a medium with 10% FBS (Gibco, #16140-071) to a final concentration ranging from 0 to 100 μM. 50 μM of diluted compounds were then added to each well (final DMSO concentration was less than 1%) and incubated under 5% CO$_2$ atmosphere at 37° C. for 120 h. After incubating, 15 μL/well of AlamarBlue (ThermoFisher, #DAL1100) reagent was added, contents of plates were mixed in an orbital shaker (Biosan, Latvia) and further incubated for 3-5 h at 37° C. under 5% CO$_2$ atmosphere. Number of living cells was estimated using a microplate spectrophotometer (Tecan Infinite M200Pro, Switzerland) measuring fluorescent signal at the excitation wavelength (λEx) of 540 nm and emission wavelength (λEm) of 590 nm.

IC$_{50}$ values were calculated using Magellan 7.2 software (Tecan, Switzerland) approximating experimental points by four-parameter logistic model with the optimization by Levenberg-Marquardt (Table 6).

The $CC_{50}$ values were determined in the test for General cytotoxicity On HepG2 cells (hepatocellular carcinoma, ATCC® HB-8065™). Cells per well were seeded in 96-well plates (Corning, #3599) at a concentration ≈20×10³ cells in 100 μL of medium and incubated for 72 h with added compounds within the range of concentrations of 200 to 0.78 μM. Cell viability was assessed using the above method. The results are given in Table 6.

TABLE 6

The results of the assessment of the specific activity of the compounds in the cell-based antiproliferative test using the target cell line panel (MV-4-11) and the results of the assessment of the general toxicity using HepG2 cell line. The Data is presented as average values of $IC_{50}$ obtained in several tests.

| Compound no. | MV-4-11 $IC_{50}$, nM | KG-1 $IC_{50}$, nM | HepG2 $CC_{50}$, μM |
|---|---|---|---|
| 3.43 | 0.5 | 0.2 | 68.1 |
| 3.44 | 0.7 | 0.7 | 65.3 |
| 3.45 | 3.4 | 0.1 | 17.4 |
| 3.46 | 0.7 | 1.1 | >100 |
| 3.47 | 1.1 | 3.3 | >100 |
| 3.48 | 3.9 | 2.7 | 31.8 |
| 3.49 | 2.8 | 12.9 | >100 |
| 3.49 × 2HCl | — | 16 | >100 |
| 3.50 | 3.8 | 26.6 | >100 |
| 3.51 | 16.9 | 12.9 | >100 |
| 3.52 | 0.9 | 1.2 | >100 |
| 3.53 | 1.3 | 2.4 | ≈90 |
| 3.54 | 15.8 | 12.2 | ≈90 |
| 3.55 | — | 6.5 | >100 |
| 3.56 | — | 13.8 | >100 |
| 3.57 | — | 17.1 | ≈90 |

The invention claimed is:
1. A compound of formula I:

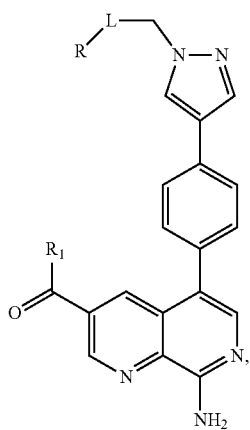

I or a pharmaceutically acceptable salt or stereoisomer thereof,
wherein L is $-[CH_2]_{0-3}-$, $-[CH_2]_{0-2}-C(O)-$, $-C(O)-[CH_2]_{0-2}-$;
R is $-NR^4R^5$, $-OR^6$;
$R^1$ is $-NR^2R^3$;
$R^2$ and $R^3$ is independently H; $C_{1-6}$ alkyl, unsubstituted or substituted by one or several substituents $R^7$; $C_{2-6}$ alkenyl, unsubstituted or substituted by one or several substituents $R^7$; $C_{2-6}$ alkynyl, unsubstituted or substituted by one or several substituents $R^7$; $C_{3-7}$ cycloalkyl, unsubstituted or substituted by one or several substituents $R^8$; $C_{3-7}$ cycloalkenyl, unsubstituted or substituted by one or several substituents $R^8$; 5-6 membered heterocyclyl with 1-2 heteroatoms, selected from N, O and/or S, unsubstituted or substituted by one or several substituents $R^9$; aryl, unsubstituted or substituted by one or several substituents $R^{10}$; heteroaryl with 1-4 heteroatoms, selected from N, O and/or S, unsubstituted or substituted by one or several substituents $R^{11}$, or $R^2$ and $R^3$ together with the nitrogen atom they are attached to, form 4-7-membered heterocyclic ring with 1-3 heteroatoms, selected from N and/or O, wherein heterocyclic ring, formed by $R^2$ and $R^3$, could be unsubstituted or substituted by one or several substituents $R^9$;

$R^4$ and $R^5$ is independently H; $C_{1-6}$ alkyl, unsubstituted or substituted by one or several substituents $R^{12}$; $C_{2-6}$ alkenyl, unsubstituted or substituted by one or several substituents $R^{12}$; $C_{2-6}$ alkynyl, unsubstituted or substituted by one or several substituents $R^{12}$; $C_{3-7}$ cycloalkyl, unsubstituted or substituted by one or several substituents $R^{13}$; $C_{3-7}$ cycloalkenyl, unsubstituted or substituted by one or several substituents $R^{13}$; 5-6 membered heterocyclyl with 1-2 heteroatoms, selected from N, O and/or S, unsubstituted or substituted by one or several substituents $R^{14}$; aryl, unsubstituted or substituted by one or several substituents $R^{15}$; heteroaryl with 1-4 heteroatoms, selected from N, O and/or S, unsubstituted or substituted by one or several substituents $R^{16}$, or $R^4$ and $R^5$ together with the nitrogen atom they are attached to, form 4-7-membered heterocyclic ring with 1-3 heteroatoms, selected from N and/or O, wherein heterocyclic ring, formed by $R^4$ and $R^5$, could be unsubstituted or substituted by one or several substituents $R^{14}$;

$R^6$ is H; $C_{1-6}$ alkyl, unsubstituted or substituted by one or several substituents $R^{17}$;

each $R^7$ and $R^{12}$ is independently H, Hal, CN, $-OR^{18}$, $-NR^{19}R^{20}$, $-C(=O)R^{18}$, $-C(=O)NR^{19}R^{20}$, $-NR^{21}C(=O)R^{18}$; $-NR^{21}C(=O) NR^{19}R^{20}$; $C_{3-7}$ cycloalkyl, unsubstituted or substituted by one or several radicals, selected from $C_{1-6}$ alkyl, halogen;

each $R^9$ and $R^{14}$ is independently H, Hal, CN, $-OR^{18}$, $-NR^{19}R^{20}$, $-C(=O)R^{18}$, $-C(=O)NR^{19}R^{20}$, $-NR^{21}C(=O)R^{18}$; $-NR^{21}C(=O) NR^{19}R^{20}$; oxo group, $C_{1-6}$ alkyl, unsubstituted or substituted by one or several halogens; $C_{3-7}$ cycloalkyl, unsubstituted or substituted by one or several radicals, selected from $C_{1-6}$ alkyl, halogen;

each $R^8$, $R^{10}$, $R^{11}$, $R^{13}$, $R^{15}$ and $R^{16}$ is independently H, Hal, CN, $-OR^{18}$, $-NR^{19}R^{20}$, $-C(=O)R^{18}$, $-C(=O)NR^{19}R^{20}$, $-NR^{21}C(=O)R^{18}$; $-NR^{21}LC(=O)NR^{19}R^{20}$; $C_1$-$C_6$ alkyl, unsubstituted or substituted by one or several halogens; $C_{3-7}$ cycloalkyl, unsubstituted or substituted by one or several radicals, selected from $C_{1-6}$ alkyl, halogen;

each $R^{17}$, $R^{18}$, $R^{19}$, $R^{20}$ and $R^{21}$ is independently H, $C_1$-$C_6$ alkyl, unsubstituted or substituted by one or several halogens; $C_2$-$C_6$ alkenyl, $C_2$-$C_6$ alkynyl, $C_3$-$C_7$ cycloalkyl, unsubstituted or substituted by one or several radicals, selected from $C_{1-6}$ alkyl, halogen; or $R^{19}$ and $R^{20}$ together with the nitrogen atom they are attached to, form 4-7-membered heterocyclic ring with 1-3 heteroatoms, selected from N and/or O, wherein the heterocyclic ring, formed by $R^{19}$ and $R^{20}$, could be unsubstituted or substituted by 1 or 2 substituents, selected from oxo group; Hal; OH; $NH_2$; CN; $C_{1-6}$ alkyl, unsubstituted or substituted by one or several halogens; $C_{1-6}$ alkoxy; $C_{1-6}$ alkylamino.

2. A compound according to claim 1, wherein L is —C(O)—, —$CH_2$—.

3. A compound according to claim 1, wherein $R^1$ is —$NR^2R^3$,
   wherein $R^2$ and $R^3$ is independently H; $C_{1-6}$ alkyl, unsubstituted or substituted by one or several substituents $R^7$; $C_{3-7}$ cycloalkyl, unsubstituted or substituted by one or several substituents $R^8$; 5-6 membered heterocyclyl with 1-2 heteroatoms, selected from N, O and/or S, unsubstituted or substituted by one or several substituents $R^9$; aryl, unsubstituted or substituted by one or several substituents $R^{10}$; heteroaryl with 1-4 heteroatoms, selected from N, O and/or S, unsubstituted or substituted by one or several substituents $R^{11}$;
   each $R^7$ and $R^9$ is independently H, Hal, CN, —$OR^{18}$, —$NR^{19}R^{20}$, —$C(=O)R^{18}$, —$C(=O)NR^{19}R^{20}$;
   each $R^8$, $R^{10}$ and $R^{11}$ is independently H, Hal, CN, —$OR^{18}$, —$NR^{19}R^{20}$, —$C(=O)R^{18}$, —$C(=O)NR^{19}R^{20}$, $C_1$-$C_6$ alkyl, unsubstituted or substituted by one or several halogens;
   each $R^{18}$, $R^{19}$ and $R^{20}$ is independently H, $C_1$-$C_6$ alkyl, unsubstituted or substituted by one or several halogens; $C_3$-$C_7$ cycloalkyl, unsubstituted or substituted by one or several radicals, selected from $C_{1-6}$ alkyl, halogen; or
   wherein $R^1$ is:

[chemical structures]

$R^{25}$ is H, $C_{1-6}$ alkyl;
$R^{26}$, $R^{27}$, $R^{28}$ are H, CN, OH, $C_{1-4}$ alkoxy;
n is 0, 1, 2, 3.

4. A compound according to claim 1, wherein R is —$NR^4R^5$, —$OR^6$;
   each $R^4$ and $R^5$ is independently H; $C_{1-6}$ alkyl, unsubstituted or substituted by one or several substituents $R^{12}$; $C_{3-7}$ cycloalkyl, unsubstituted or substituted by one or several substituents $R^{13}$; 5-6 membered heterocyclyl with 1-2 heteroatoms, selected from N, O and/or S, unsubstituted or substituted by one or several substituents $R^{14}$; aryl, unsubstituted or substituted by one or several substituents $R^{15}$; heteroaryl with 1-4 heteroatoms, selected from N, O and/or S, unsubstituted or substituted by one or several substituents $R^{16}$;
   each $R^{12}$ and $R^{14}$ is independently H, Hal, CN, —$OR^{18}$, —$NR^{19}R^{20}$, —$C(=O)R^{18}$, —$C(=O)NR^{19}R^{20}$;
   each $R^{13}$, $R^{15}$ and $R^{16}$ is independently H, Hal, CN, —$OR^{18}$, —$NR^{19}R^{20}$, —$C(=O)R^{18}$, —$C(=O)NR^{19}R^{20}$, $C_1$-$C_6$ alkyl, unsubstituted or substituted by one or several halogens;
   each $R^{18}$, $R^{19}$ and $R^{20}$ is independently H, $C_1$-$C_6$ alkyl, unsubstituted or substituted by one or several halogens; $C_3$-$C_7$ cycloalkyl, unsubstituted or substituted by one or several radicals, selected from $C_{1-6}$ alkyl, halogen; or
   wherein $R^4$ and $R^5$ together with the nitrogen atom they are attached to, form 4-7-membered heterocyclic ring with 1-3 heteroatoms, selected from N and/or O, wherein heterocyclic ring, formed by $R^4$ and $R^5$, could be unsubstituted or substituted by one or several substituents $R^{14}$,
   wherein the 4-7-membered heterocyclic ring is

[chemical structures]

$R^{25}$ is H, $C_{1-6}$ alkyl;
$R^{28}$ are H, CN, OH, $C_{1-4}$ alkoxy;
n is 0, 1, 2, 3;
$R^6$ is $C_{1-6}$ alkyl, unsubstituted or substituted by one or several halogens.

5. A compound according to claim 1, wherein $R^1$ is:

[chemical structures]

6. A compound according to claim 1, wherein R is:

[chemical structures]

7. A compound according to claim 1, wherein the compound is:
8-Amino-N-(cyclopropylmethyl)-5-(4-(1-(2-(dimethylamino)-2-oxoethyl)-1H-pyrazole-4-yl)phenyl)-1,7-naphthyridine-3-carboxamide (3.43);
8-amino-N-(cyclopropylmethyl)-5-(4-(1-(2-(4-methylpiperazin-1-yl)-2-oxoethyl)-1H-pyrazole-4-yl)phenyl)-1,7-naphthyridine-3-carboxamide (3.44);
8-amino-N-(cyclopropylmethyl)-5-(4-(1-(2-methoxyethyl)-1H-pyrazole-4-yl)phenyl)-1,7-naphthyridine-3-carboxamide (3.45);
8-amino-N-cyclopropyl-5-(4-(1-(2-(dimethylamino)-2-oxoethyl)-1H-pyrazole-4-yl)phenyl)-1,7-naphthyridine-3-carboxamide (3.46);
8-amino-N-cyclopropyl-5-(4-(1-(2-(4-methylpiperazin-1-yl)-2-oxoethyl)-1H-pyrazole-4-yl)phenyl)-1,7-naphthyridine-3-carboxamide (3.47);
8-amino-N-cyclopropyl-5-(4-(1-(2-methoxyethyl)-1H-pyrazole-4-yl)phenyl)-1,7-naphthyridine-3-carboxamide (3.48);
2-(4-(4-(8-amino-3-(4-methylpiperazine-1-carbonyl)-1,7-naphthyridine-5-yl)phenyl)-1H-pyrazole-1-yl)-N,N-dimethylacetamide (3.49);
2-(4-(4-(8-amino-3-(4-methylpiperazine-1-carbonyl)-1,7-naphthyridine-5-yl)phenyl)-1H-pyrazole-1-yl)-N,N-dimethylacetamide dihydrochloride (3.49×2HCl)

2-(4-(4-(8-amino-3-(4-methylpiperazine-1-carbonyl)-1,7-naphthyridine-5-yl)phenyl)-1H-pyrazole-1-yl)-1-(4-methylpiperazine-1yl)ethan-1-one (3.50);

(8-amino-5-(4-(1-(2-methoxyethyl)-1H-pyrazole-4-yl)phenyl)-1,7-naphthyridin-3-yl)(4-methylpiperazine-1-yl)methanone (3.51);

2-(4-(4-(8-amino-3-(azetidine-1-carbonyl)-1,7-naphthyridine-5-yl)phenyl)-1H-pyrazole-1-yl)-N,N-dimethylacetamide (3.52);

2-(4-(4-(8-amino-3-(azetidine-1-carbonyl)-1,7-naphthyridine-5-yl)phenyl)-1H-pyrazole-1-yl)-1-(4-methylpiperazine-1-yl)ethan-1-one (3.53);

(8-amino-5-(4-(1-(2-methoxyethyl)-1H-pyrazole-4-yl)phenyl)-1,7-naphthyridin-3-yl) (azetidin-1-yl)methanone (3.54);

8-amino-5-(4-(1-(2-(dimethylamino)-2-oxoethyl)-1H-pyrazole-4-yl)phenyl-N-(2-methoxyethyl)-N-methyl-1,7-naphthyridine-3-carboxamide (3.55);

8-amino-N-(2-methoxyethyl)-N-methyl-5-(4-(1-(2-(4-methylpiperazine-1-yl)-2-oxoethyl)-1H-pyrazole-4-yl)phenyl)-1,7-naphthyridine-3-carboxamide (3.56);

8-amino-N-(2-methoxyethyl)-5-(4-(1-(2-methoxyethyl)-1H-pyrazole-4-yl)phenyl)-N-methyl-1,7-naphthyridine-3-carboxamide (3.57).

8. A method for inhibiting biological activity of cyclin-dependent protein kinases CDK8/19 in a subject, comprising contacting the cyclin-dependent protein kinases CDK8/19 with the compound according to claim 1.

9. A pharmaceutical composition, comprising the compound according to claim 1, or a pharmaceutically acceptable salt or stereoisomer thereof, and one or more pharmaceutically acceptable excipients.

10. The pharmaceutical composition according to claim 9, wherein the pharmaceutical composition is for the prevention or treatment of a disease or disorder mediated by the activation of cyclin-dependent protein kinases CDK8/19.

11. A pharmaceutical composition according to claim 10 for the prevention or treatment of a disease or disorder mediated by the activation of cyclin-dependent protein kinases CDK8/19, wherein the disease or disorder mediated by the activation of cyclin-dependent protein kinases CDK8/19 is an oncological or haemato-oncological disease.

12. A pharmaceutical composition according to claim 11, wherein the oncological or haemato-oncological disease is selected from the group comprising colorectal cancer, melanoma, breast cancer, triple-negative breast cancer (TNBC), prostate cancer, metastatic ovarian cancer, metastatic stomach cancer, leucosis, acute myeloid leukemia, pancreatic cancer.

13. A method for treating a disease or disorder mediated by the activation of cyclin-dependent protein kinases CDK8/19 comprising administering a therapeutically effective amount of the compound according to claim 1, or pharmaceutically acceptable salt thereof, or a pharmaceutical composition comprising a therapeutically effective amount of the compound according to—claim 1, or pharmaceutically acceptable salt thereof, and one or more pharmaceutically acceptable excipients, to a subject in need thereof.

14. A method for treating a disease or disorder according to claim 13, wherein the disease or disorder mediated by the activation of cyclin-dependent protein kinases CDK8/19 is an oncological or haemato-oncological disease.

15. A method for treating a disease according to claim 14, wherein the oncological or haemato-oncological disease is selected from the group comprising colorectal cancer, melanoma, breast cancer, triple-negative breast cancer (TNBC), prostate cancer, metastatic ovarian cancer, metastatic stomach cancer, leucosis, acute myeloid leukemia, pancreatic cancer.

\* \* \* \* \*